(12) United States Patent
Richter et al.

(10) Patent No.: US 6,440,165 B1
(45) Date of Patent: *Aug. 27, 2002

(54) BIFURCATED STENT WITH IMPROVED SIDE BRANCH APERTURE AND METHOD OF MAKING SAME

(75) Inventors: Jacob Richter, Ramat Hasharon; Gregory Pinchasik, Herzlia, both of (IL)

(73) Assignee: Medinol, Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/575,957

(22) Filed: May 23, 2000

Related U.S. Application Data

(63) Continuation-in-part of application No. 09/072,846, filed on May 5, 1998, now Pat. No. 6,251,133, and a continuation-in-part of application No. 08/642,297, filed on May 3, 1996, now abandoned.

(51) Int. Cl.[7] ................................................. A61F 2/06
(52) U.S. Cl. ..................................... 623/1.35; 623/1.16
(58) Field of Search ............................... 623/1.16, 1.35, 623/1.15, 1.25, 1.3; 606/194

(56) References Cited

U.S. PATENT DOCUMENTS

| | | | | |
|---|---|---|---|---|
| 5,755,734 A | * | 5/1998 | Richter et al. | 606/194 |
| 5,755,735 A | * | 5/1998 | Richter et al. | 606/194 |
| 5,824,052 A | * | 10/1998 | Khosravi et al. | 623/1.15 |
| 5,827,320 A | * | 10/1998 | Richter et al. | 606/194 |
| 5,906,640 A | * | 5/1999 | Penn et al. | 623/1.35 |
| 6,096,073 A | | 8/2000 | Webster et al. | |
| 6,165,195 A | | 12/2000 | Wilson et al. | |
| 6,251,133 B1 | * | 6/2001 | Richter et al. | 623/1.16 |

FOREIGN PATENT DOCUMENTS

| | | |
|---|---|---|
| EP | 0 551 179 | 7/1993 |
| EP | 0 916 317 | 5/1999 |
| WO | WO 00/44307 | 8/2000 |

* cited by examiner

Primary Examiner—David H. Willse
Assistant Examiner—Suzette J. Jackson
(74) Attorney, Agent, or Firm—Kenyon & Kenyon

(57) ABSTRACT

A stent for insertion into a blood vessel is made from a sheet having a longitudinal axis and a first portion and a second portion. The first portion has a proximal end and a distal end and a first lateral side and a second lateral side with the lateral sides of the first portion substantially parallel to the longitudinal axis and disposed apart from each other a first distance. The second portion has a proximal end and a distal end and a first lateral side and a second lateral side with the lateral sides of the second portion substantially parallel to the longitudinal axis and disposed apart from each other a second distance that is less than the first distance. The proximal end of the second portion communicates with the distal end of the first portion. The first lateral side of the first portion is connected to the second lateral side of the first portion and the first lateral side of the second portion is connected to the second lateral side of the second portion to form the stent. A portion of the distal end of the first portion and a portion of the proximal end of the second portion define a side branch aperture.

4 Claims, 21 Drawing Sheets

BIFURCATED STENT WITH IMPROVED SIDE BRANCH APERTURE AND METHOD OF MAKING SAME

This application is a continuation-in-part of U.S. Ser. No. 09/072,846, filed May 5, 1998, which issued as U.S. Pat. No. 6,251,133 on Jun. 26, 2001 and U.S. Ser. No. 08/642,297 filed May 3, 1996 which is abandoned.

FIELD OF THE INVENTION

The present invention relates to stents, and more particularly to bifurcated stents and methods of making bifurcated stents for insertion within a branching vessel.

BACKGROUND OF THE INVENTION

Stents are well known in the art. They are typically formed of a cylindrical metal mesh which can expand when pressure is internally applied. Alternatively, they can be formed of wire wrapped into a cylindrical shape or sheets of material formed into a cylindrical shape.

Stents are devices which are usually implanted within bodily conduits including the vascular system to reinforce collapsing, partially occluded, weakened, or abnormally dilated sections of the blood vessel. Stents also have been successfully implanted in other areas, e.g., the urinary tract or the bile duct to reinforce such bodily conduits.

U.S. Pat. No. 4,994,071 (MacGregor) discloses an expandable, bifurcating stent having a main cylindrical lattice formed from interconnected flexible wire. Two additional cylindrical lattices, having smaller diameters than the main lattice, are similarly constructed. The main lattice includes a flexible wire interconnecting the main lattice to one of the additional lattices. A second flexible wire interconnects the main lattice to the other additional lattice. The flexible wires form backbones that extend axially along the length of the main lattice and along each of the additional lattices. One disadvantage of this bifurcating stent is the complex nature of the interconnection of the flexible wires forming the backbones with the loop structure of each lattice.

SUMMARY OF THE INVENTION

The present invention solves these and other disadvantages of the prior art by providing bifurcated stents and methods of fabricating and deploying bifurcated stents having a stem portion and two leg portions.

In a first embodiment of the invention, a bifurcated stent is made by providing three sheets patterned to a desired pattern, wherein two sheets are substantially the same size and the third sheet is wider than either of the first two sheets. Each of the sheets is formed into tubes by turning up the longitudinal edges and forming a joint by welding. The larger sheet forms a tube that acts as the stem portion of the bifurcated stent and the other sheets form tubes which act as the leg portions of the bifurcated stent. The two leg portions are then joined to the stem portion to form the bifurcated stent.

In a second embodiment of the invention, the bifurcated stent is formed by preparing two stent sheets. For each sheet, the longitudinal edges of a portion of the sheet are turned up and secured to each other to form one of the two leg portions of the bifurcated stent. The remaining free edges of each of the two sheets are then joined to form the stem portion of the stent.

In a third embodiment, the bifurcated stent comprises first and second tubular portions. The first portion has a proximal end which forms the stem portion and a distal end which forms one of the leg portions of the bifurcated stent. A branch aperture is disposed between the proximal end and the distal end of the first portion. The second portion is introduced into the longitudinal bore of the stem portion of the first portion and is advanced through the branch aperture so that it protrudes beyond the branch aperture to form a second leg. When the second portion is expanded, the proximal end of the second portion engages the material defining the branch aperture so as to secure the second leg in the desired position. It is an object of this invention to provide a method of making a bifurcated stent, comprising the steps of: a) preparing a first sheet having a first edge, a second edge, a third edge, and a fourth edge; b) preparing a second sheet having a first edge, a second edge, a third edge, and a fourth edge; c) preparing a third sheet having a first edge, a second edge, a third edge, and a fourth edge; d) attaching the second edge to the third edge of the first sheet to form a tubular first leg portion having a proximal end and a distal end; e) attaching the second edge to the third edge of the second sheet to form a tubular second leg portion having a proximal end and a distal end; f) attaching the second edge to the third edge of the third sheet to form a tubular stem portion having a proximal end and a distal end; and g) attaching the proximal end of the first leg portion and the proximal end of the second leg portion to the distal end of the stem portion.

It is another object of this invention to provide a method of making a bifurcated stent, comprising the steps of a) preparing a first sheet having a proximal end and a distal end; b) deforming the distal end of the first sheet to form a first leg and deforming the proximal end of the first sheet to form a first stem half; c) preparing a second sheet having a proximal end and a distal end; d) deforming the distal end of the second sheet to form a second leg and deforming the proximal end of the second sheet to form a second stem half; and e) joining the first stem half to the second stem half to form a stem.

It is yet another object of this invention to provide a method of making a bifurcated stent comprising the steps of a) preparing a first expandable tubular member having a proximal end and a distal end and a longitudinal bore therethrough, the first tubular member provided with a branch aperture disposed between said proximal end and the distal end, the branch aperture communicating with said longitudinal bore and the aperture sized and adapted to receive and secure a second expandable tubular member; b) delivering the first expandable tubular member to a bifurcated vessel having a first lumen and a second lumen so that the first expandable member is disposed within the first lumen and the branch aperture communicates with the second lumen; c) expanding the first expandable member in an amount sufficient to secure the first expandable member in the first lumen; d) preparing a second expandable tubular member having a proximal end and a distal end and having longitudinal bore therethrough; e) widening the branch aperture; f) delivering the second expandable tubular member into the branch aperture so that the distal end of the second expandable tubular member is disposed within the second lumen and the proximal end of the second expandable tubular member is disposed within the longitudinal bore of the first longitudinal member; and g) expanding the second expandable tubular member in an amount sufficient to secure the second expandable tubular member within the second lumen and within said branch aperture.

It is still another object of this invention to provide a method of making a bifurcated stent comprising the steps of:

a) preparing a sheet having a proximal end, a distal end, a longitudinal axis, and a circumferential axis, the sheet provided with:
  a first side having a proximal portion having a proximal end and a distal end and a distal portion having a proximal end and a distal end;
  a second side having a proximal end and a distal end, the second side disposed between the proximal end of the sheet and the distal end of the sheet;
  a third side having a proximal end and a distal end, the third side disposed between the distal end of the second side and the distal end of the sheet;
  a fourth side disposed between the proximal end of the proximal portion of the first side and the proximal end of the second side;
  a fifth side disposed between the distal end of the distal portion of the first side and the distal end of the third side, the fifth side having a length that is shorter than the length of the fourth side; and
  a sixth side disposed between the second side and the third side;
b) attaching the second side to the proximal portion of the first side and attaching the third side to the distal portion of the first side to form a first expandable tubular member having a longitudinal bore defining a longitudinal axis, the fourth side defining a proximal stent aperture communicating with the longitudinal bore, the fifth side defining a distal stent aperture communicating with the longitudinal bore, and the sixth side and the proximal end of the third side and the proximal end of the distal portion of the first side defining a side branch aperture communicating with the longitudinal bore and sized and adapted to receive and secure a second expandable tubular member;
c) delivering the first expandable tubular member to a bifurcated vessel having a first lumen and a second lumen so that the first expandable tubular member is disposed within the first lumen and the branch aperture communicates with the second lumen;
d) expanding the first expandable tubular member in an amount sufficient to secure the first expandable tubular member in the first lumen;
e) preparing a second expandable tubular member having a proximal end and a distal end and having longitudinal bore therethrough;
f) delivering the second expandable tubular member into the branch aperture of the first tubular member so that the distal end of the second expandable tubular member is disposed within the second lumen and the proximal end of the second expandable tubular member is disposed within the longitudinal bore of the first tubular member; and
g) expanding the second expandable tubular member in an amount sufficient to secure the second expandable tubular member within the second lumen and within the branch aperture.

It is yet another object of this invention to provide a bifurcated stent comprising:
a) a first tubular member having a proximal end and a distal end and a longitudinal bore therethrough defining a longitudinal axis, the first tubular member comprised of a sheet having a proximal end, a distal end, a longitudinal axis, and a circumferential axis, the sheet provided with:
  a first side having a proximal portion having a proximal end and a distal end and a distal portion having a proximal end and a distal end;
  a second side having a proximal end and a distal end, the second side disposed between the proximal end of the sheet and the distal end of the sheet;
  a third side having a proximal end and a distal end, the third side disposed between the distal end of the second side and the distal end of the sheet;
  a fourth side disposed between the proximal end of the proximal portion of the first side and the proximal end of the second side;
  a fifth side disposed between the distal end of the distal portion of the first side and the distal end of the third side, the fifth side having a length that is shorter than the length of the fourth side; and
  a sixth side disposed between the second side and the third side;
b) means for attaching the second side to the proximal portion of the first side and the third side to the distal portion of the first side so that the fourth side defines a proximal stent aperture communicating with the longitudinal bore, the fifth side defines a distal stent aperture communicating with the longitudinal bore, and the sixth side and the proximal end of the third side and the proximal end of the distal portion of the first side define a side branch aperture communicating with the longitudinal bore and sized and adapted to receive and secure a second tubular member; and
c) a second tubular member having a proximal end and a distal end and having longitudinal bore therethrough, the second tubular member disposed within the branch aperture so that the proximal end of the second tubular member is disposed within the longitudinal bore of the first tubular member.

It is a further object of this invention to provide a method of making a bifurcated stent comprising the steps of:
a) cutting a proximal member from a first expandable tube having a first cross-sectional diameter, the proximal member having a proximal end and a distal end and a longitudinal bore therethrough;
b) cutting a distal member from a second expandable tube having a second cross-sectional diameter smaller than the first diameter of the first tube, the distal member having a proximal end and a distal end and a longitudinal bore therethrough;
c) attaching a portion of the distal end of the proximal member to a portion of the proximal end of the distal member so that the longitudinal bore of the proximal member is in fluid communication with the longitudinal bore of the distal member to form a first expandable tubular member having a proximal end and a distal end and a longitudinal bore therethrough, the unattached portion of the distal end of the proximal member and the unattached portion of the proximal end of the distal member defining a side branch aperture communicating with the longitudinal bore of the first tubular member and sized and adapted to receive and secure a second expandable tubular member;
c) delivering the first expandable tubular member to a bifurcated vessel having a first lumen and a second lumen so that the first expandable tubular member is disposed within the first lumen and the branch aperture communicates with the second lumen;
d) expanding the first expandable tubular member in an amount sufficient to secure the first expandable tubular member in the first lumen;
e) preparing a second expandable tubular member having a proximal end and a distal end and having longitudinal bore therethrough;

f) delivering the second expandable tubular member into the branch aperture of the first tubular member so that the distal end of the second expandable tubular member is disposed within the second lumen and the proximal end of the second expandable tubular member is disposed within the longitudinal bore of the first tubular member; and g) expanding the second expandable tubular member in an amount sufficient to secure the second tubular member within the second lumen and within the branch aperture.

It is yet a further object of this invention to provide a bifurcated stent comprising:

a) a first tubular member having a proximal end and a distal end and a longitudinal bore therethrough, the first tubular member comprised of a proximal member and a distal member, the proximal member having a first cross-sectional diameter, a proximal end and a distal end and a longitudinal bore therethrough, and the distal member having a second cross-sectional diameter smaller than the first diameter, a proximal end and a distal end and a longitudinal bore therethrough;

b) means for attaching a portion of the distal end of the proximal member to a portion of the proximal end of the distal member so that the longitudinal bore of the proximal member is in fluid communication with the longitudinal bore of the distal member to form the first tubular member, the unattached portion of the distal end of the proximal member and the unattached portion of the proximal end of the distal member defining a side branch aperture communicating with the longitudinal bore of the first tubular member and sized and adapted to receive and secure a second expandable tubular member; and c) a second tubular member having a proximal end and a distal end and having longitudinal bore therethrough, the second tubular member disposed and secured within the branch aperture so that the proximal end of the second tubular member is disposed within the longitudinal bore of the first tubular member.

DETAILED DESCRIPTION

Figure 1:
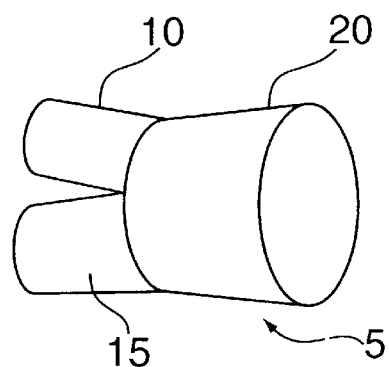
FIG. 1 shows a bifurcated stent manufactured in accordance with the present invention.
Figure 2:
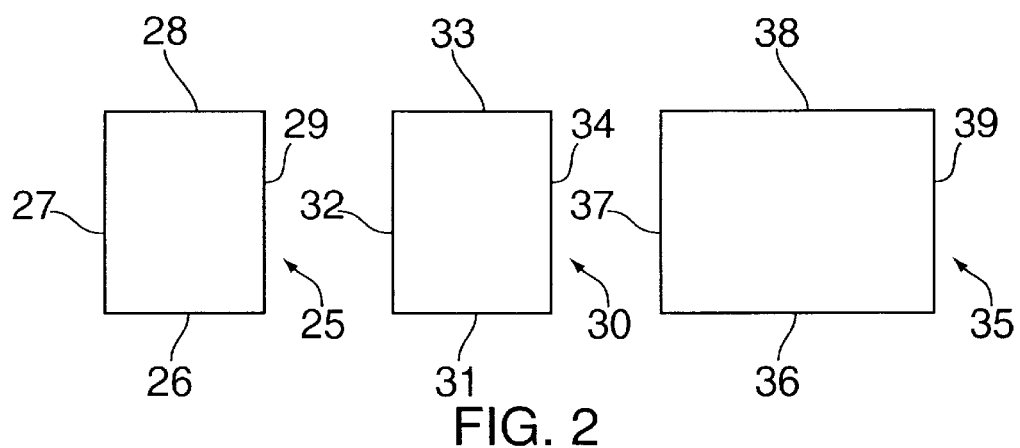
FIG. 2 shows sheets used to form the legs and stem of the stent shown in FIG. 1.
Figure 3:
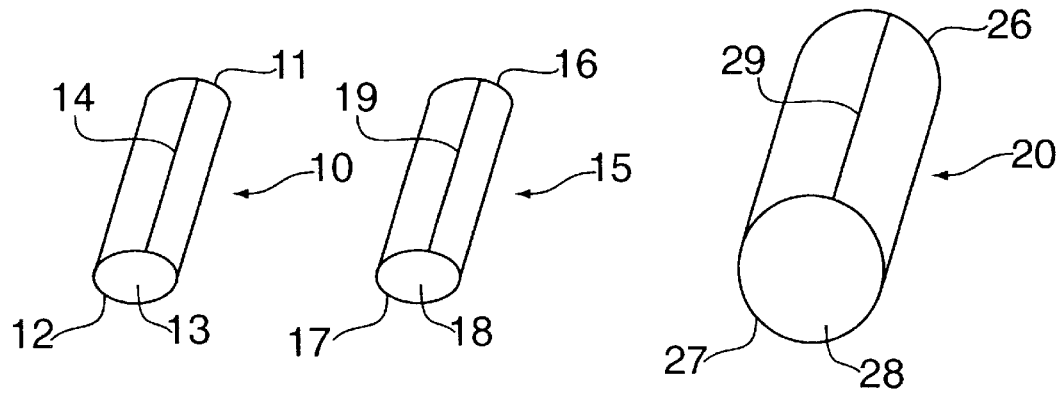
FIG. 3 shows the sheets shown in FIG. 2 after they have been rolled into a tubular shape.
Figure 4:
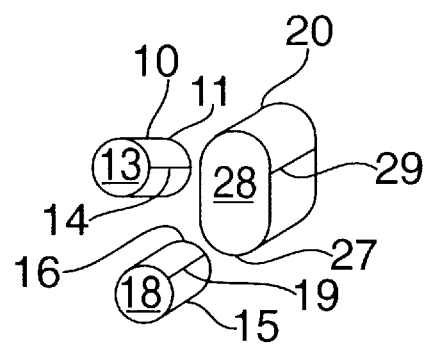
FIG. 4 is a perspective view of the tubes shown in FIG. 3 prior to assembly.
Figure 5:
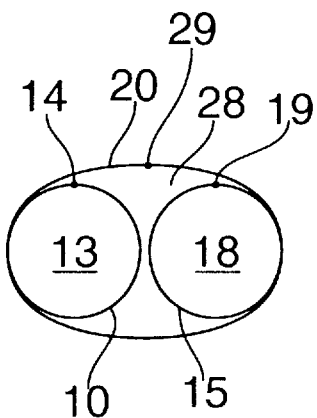
FIG. 5 is an end view of the tubes shown in FIGS. 3 and 4 after they have been assembled to form a stent.
Figure 6:
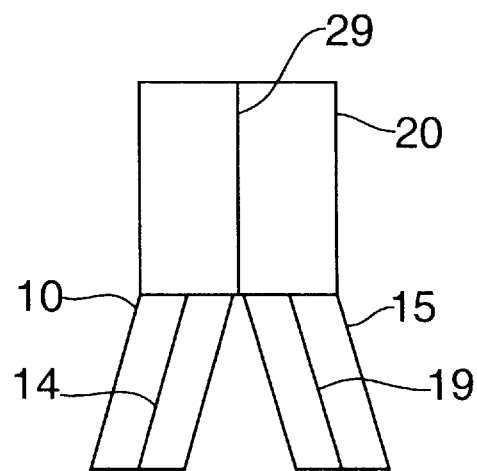
FIG. 6 is a top view of the assembled apparatus shown in FIG. 5.

In the embodiment illustrated in FIG. 1, the bifurcation stent 5 comprises a first leg 10, a second leg 15, and a stem 20. FIG. 2 shows a first sheet 25 which is used to form first leg 10, a second sheet 30 which is used to form second leg 15, and a third sheet 35 which is used to form stem 20. The first sheet 25 and second sheet 30 are substantially flat and are sized to a predetermined length and width. For many applications, the first sheet 25 and second sheet 30 will have substantially the same dimensions so as to produce legs 10 and 15 that are substantially the same size, however, the legs 10 and 15, and the sheets 25 and 30 used to produce them, may be of varying sizes as specific applications dictate. The stents of this invention may be sized so that when assembled they are their final size, however, in a preferred embodiment the stents are expandable and sized and adapted to assume their final dimensions upon expansion. The stent sheets 70 and 75 may be patterned or etched with perforations forming a variety of patterns as specific applications dictate to achieve the expandable features required as previously discussed. The third sheet 35 is sized so that when it is rolled into a tube its internal cross-section can be made to accommodate the cross-sectional external diameters of first leg 10 and second leg 15. First sheet 25 has a first edge 26, a second edge 27, a third edge 28, and a fourth edge 29. Second sheet 30 has a first edge 31, a second edge 32, a third edge 33, and a fourth edge 34. Third sheet 35 has a first edge 36, a second edge 37, a third edge 38, and a fourth edge 39. After the sheet metal has been cut to form sheets 25, 30, and 35, it is deformed and rolled so as to cause two opposite edges to meet and create a cylinder. In the example shown in FIGS. 2 and 3, edge 27 is joined to edge 29 via weld run 14 to form first leg 10. Edge 32 is joined to edge 34 via weld run 19 to form second leg 15. Edge 37 is joined to edge 39 via weld run 29 to form stem 20. The edges may be joined in a wide variety of ways well known to those skilled in the art as suitable for this purpose, e.g., screwing, crimping, soldering, however, in a preferred embodiment welding is utilized. In an especially preferred embodiment, spot welding is utilized. As shown in FIG. 3, first leg 10 has a proximal end 11, a distal end 12, and defines a longitudinal bore 13. Second leg 15 has a proximal end 16, a distal end 17, and defines a longitudinal bore 18. The stem 20 has a proximal end 26, a distal end 27, and defines a longitudinal bore 28. FIG. 4 shows the first leg 10, second leg 15, and stem 20 just prior to assembly. To form the bifurcated stent 5, the proximal end 11 of first leg 10 and the proximal end 16 of second leg 15 are joined to the distal end 27 of the stem portion 20 so that the longitudinal bores 13, 18, and 28 are in communication with each other. FIG. 5 is an end view and FIG. 6 is a side view of the assembled apparatus.

Figure 7:
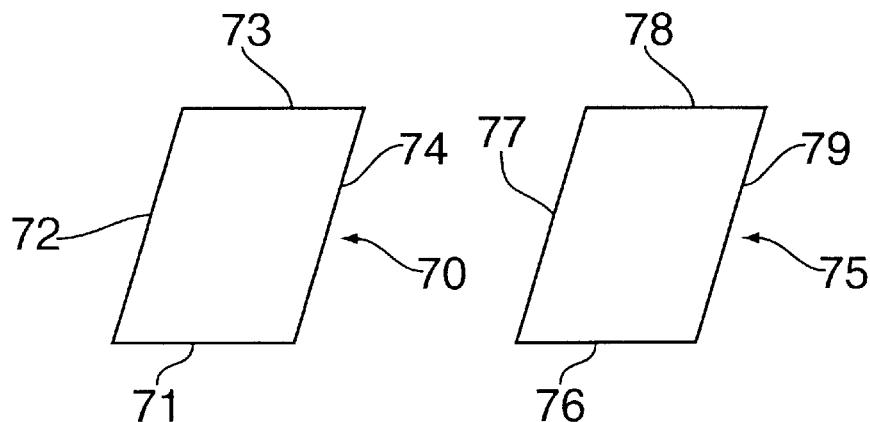
FIG. 7 shows sheets used to form another embodiment of a bifurcated stent manufactured in accordance with the invention.
Figure 8:
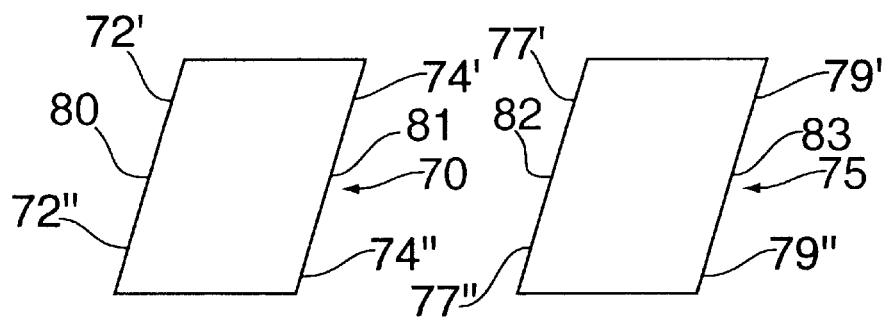
FIG. 8 shows the sheets of FIG. 7 with demarcation points.
Figure 11:
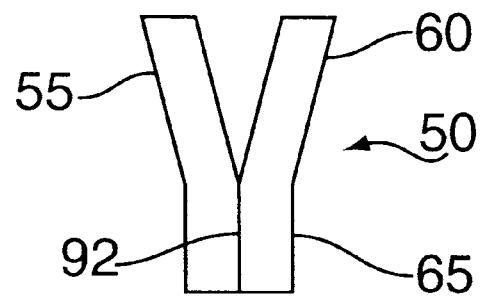
FIG. 11 is a side view of the tubes shown in FIGS. 9 and 10 after assembly.

FIG. 11 shows a second embodiment of a bifurcation stent manufactured in accordance with this invention. The stent 50 is provided with a first leg 55 and a second leg 60 attached to a stem portion 65. The bifurcation stent 50 is formed from a first sheet 70 and a second sheet 75 as shown in FIG. 7. The stent sheets 70 and 75 may be patterned or etched with perforations forming a variety of patterns as specific applications dictate to achieve the expandable features required as previously discussed. The sheets 70 and 75 are substantially flat and have a predetermined length and width. First sheet 70 has a first edge 71, a second edge 72, a third edge 73 and a fourth edge 74. The second sheet 75 has a first edge 76, a second edge 77, a third edge 78, and a fourth edge 79. To form the legs of the stent a portion of edge 72 is rolled towards a portion of edge 74 and a portion of edge 77 is rolled towards a portion of edge 79. Demarcation points 80, 81, 82, and 83 are selected on sheets 70 and 75 as shown in FIG. 8. These demarcation points 80, 81, 82, and 83 are selected to meet the requirement of specific applications and may be adjusted depending upon the length required for legs 55 and 60 and the length required for stem 65. Demarcation points 80 and 81 that are equidistant from edges 73 and 71 and demarcation points 82 and 83 that are equidistant from edges 76 and 78 will result in a stent in which the legs 55 and 60 have a length that is substantially equal to stem portion 65. If the demarcation points are selected to be closer to edges 73 and 78 than to edges 71 and 76 the stem will have a length that is greater than the length of each of the legs. If the demarcation points are selected to be closer to edges 71 and 76 than to edges 73 and 78, each of the legs 60 and 65 will have a length that is greater than the length of the stem 65. In a preferred embodiment, however, the demarcation points 80, 81, 82, and 83, are selected so that proximal edges 72", 74", 77", and 79" are about ⅓ the length of edges 72, 74, 77, and 79. As shown in FIG. 8, demarcation point 80 divides edge 72 at approximately its midpoint into a distal edge 72', and a proximal edge 72". Demarcation point 81 divides edge 74 at approximately its midpoint into a distal edge 74', and a proximal edge 74". Demarcation point 82 divides edge 77 at approximately its midpoint into a distal edge 77' and a proximal edge 77" and demarcation point 83 divides edge 79 at approximately its midpoint into a distal edge 79' and a proximal edge 79".

Figure 9:
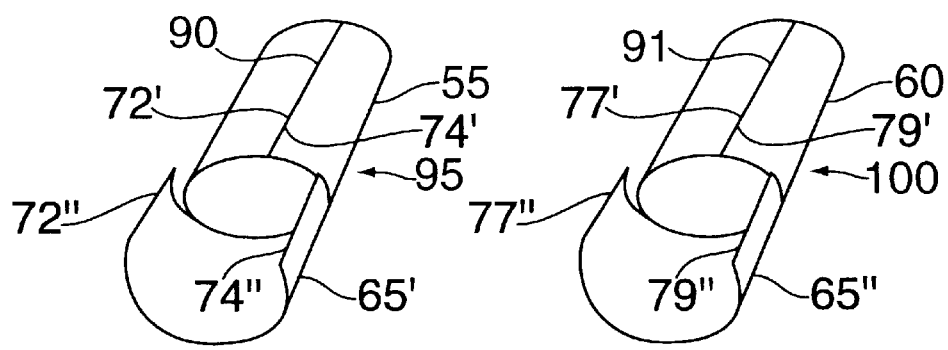
FIG. 9 shows the sheets of FIG. 8 after they have been rolled into a tubular shape.
Figure 10B:
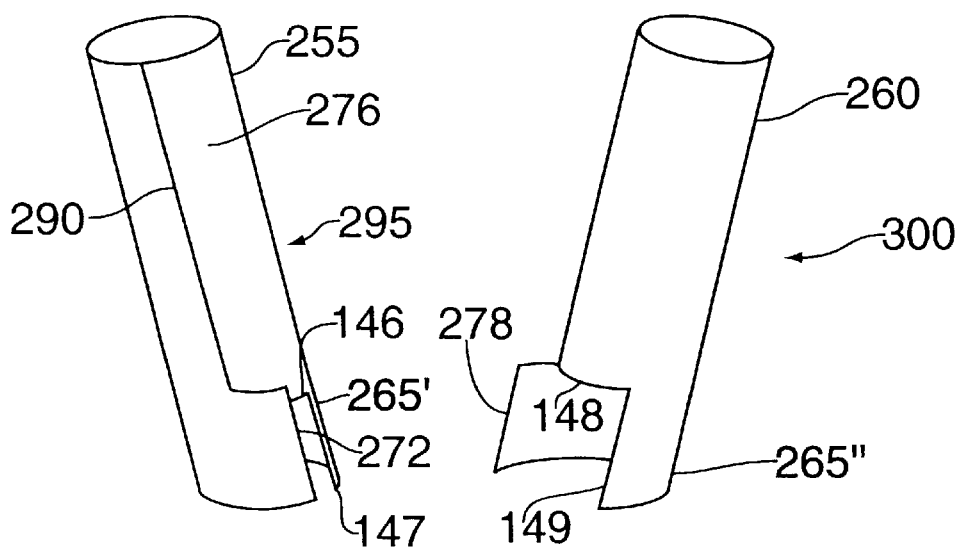
FIG. 10B shows the tubes of FIG. 9B just prior to assembly.
Figure 10:
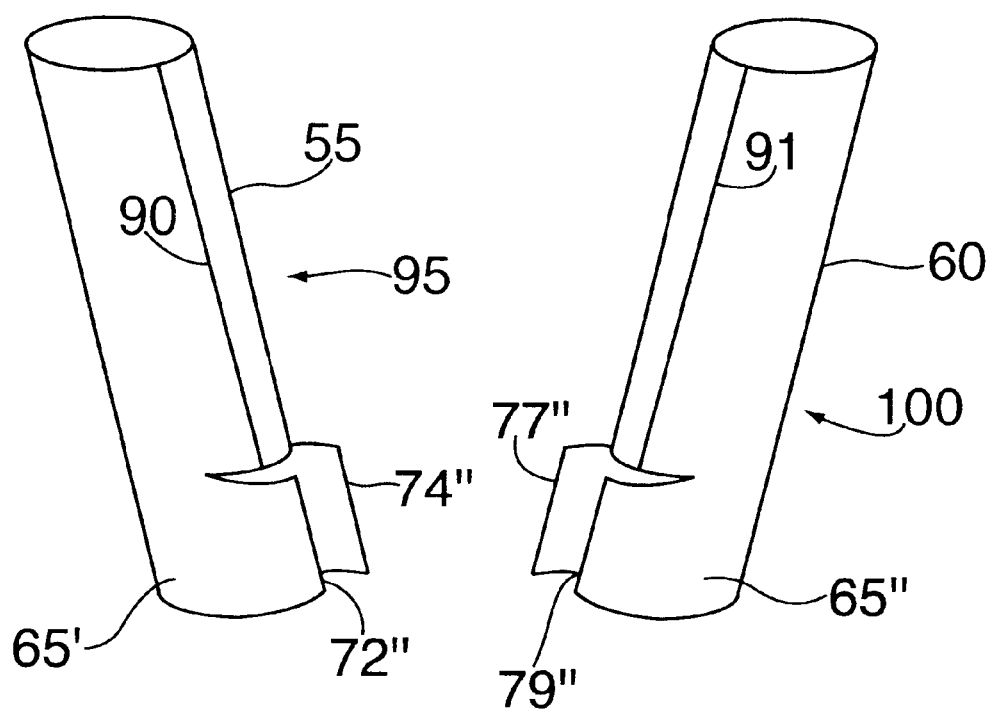
FIG. 10 shows the tubes of FIG. 9 just prior to assembly.
Figure 12B:
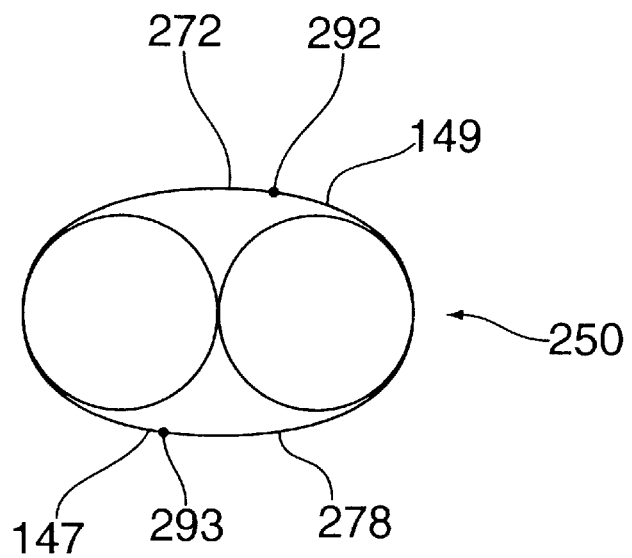
FIG. 12B is an end view of the assembled apparatus shown in FIG. 11B.
Figure 12C:
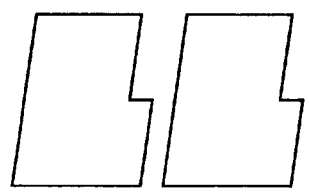
FIG. 12C shows an alternative embodiment of a pattern that may be used in place of the patterns shown in FIGS. 7 and 7B.
Figure 12:
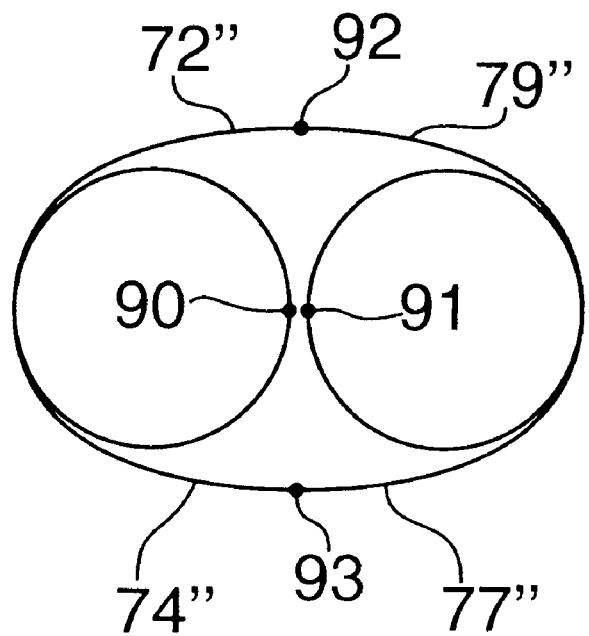
FIG. 12 is an end view of the assembled apparatus shown in FIG. 11.

To form the stent, edge 72' is connected to edge 74' via weld run 90 to form first member 95 having a first leg portion 55 and a first stem half 65' as shown in FIG. 9. Edge 77' is connected to edge 79' via weld run 91 to form second member 100 having a second leg portion 60 and a second stem half 65". As previously discussed, the edges may be connected in a variety of ways well known to those skilled in the art. FIG. 10 shows the first member 95 and the second member 100 shown in FIG. 9 in alignment just prior to assembly. To produce the bifurcated stent 50 shown in FIGS. 11 and 12, edge 72" is connected to edge 79" via weld run 92 and edge 74" is connected to edge 77" via weld run 93 so that first stem half 65' and second stem half 65" form stem 65. FIG. 12 is a cross-sectional end view of the stent shown in FIG. 11.

Figure 7B:
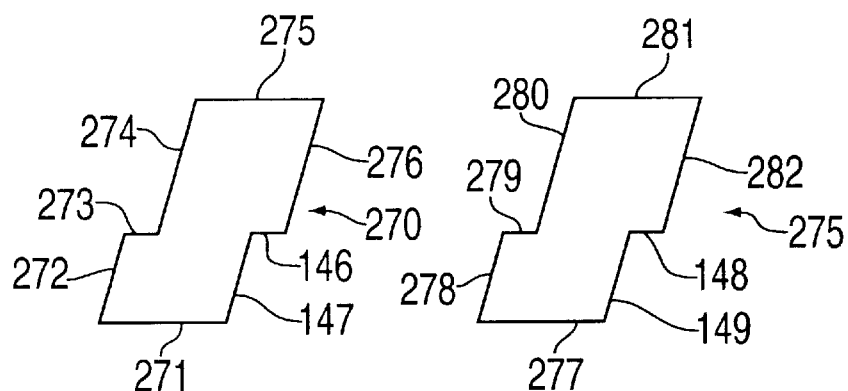
FIG. 7B shows sheets used to form another embodiment of a bifurcated stent manufactured in accordance with the invention.
Figure 11B:
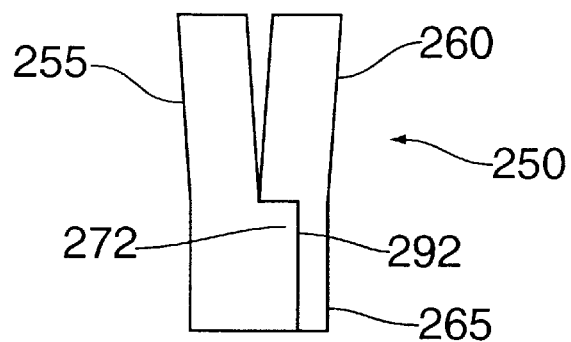
FIG. 11B is a side view of the tubes shown in FIGS. 9B and 10B after assembly.

In the embodiment shown in FIG. 7, sheets 70 and 75 are squares or rectangles. The sheets 70 and 75 are not limited to this configuration, however, as shown in FIG. 7B. FIG. 11B shows a bifurcation stent manufactured using the sheets 270 and 275 shown in FIG. 7B. The stent 250 is provided with a first leg 255 and a second leg 260 attached to a stem portion 265.

Figure 9B:
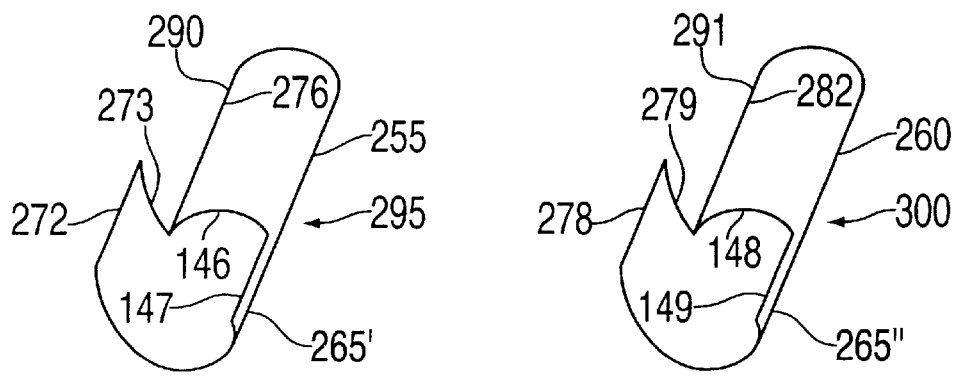
FIG. 9B shows the sheets of FIG. 7B after they have been rolled into a tubular shape.

The bifurcation stent 250 is formed from a first sheet 270 and a second sheet 275 as shown in FIG. 7B. The stent sheets 270 and 275 may be sized and etched as previously discussed. As shown in FIG. 7B, first sheet 270 has a first edge 271, a second edge 272, a third edge 273, a fourth edge 274, a fifth edge 275, and a sixth edge 276, a seventh edge 146, and an eighth edge 147. The second sheet 275 has a first edge 277, a second edge 278, a third edge 279, a fourth edge 280, a fifth edge 281, a sixth edge 282, a seventh edge 148, and an eighth edge 149. As shown in FIG. 9B, edge 274 is connected to edge 276 via weld run 290 to form first member 295 having a first leg portion 255 and a first stem half 265'. Edge 280 is connected to edge 282 via weld run 291 to form second member 300 having a second leg portion 260 and a second stem half 265". As previously discussed, the edges may be connected in a variety of ways well known to those skilled in the art. FIG. 10B shows the first member 295 and the second member 300 shown in FIG. 9B in alignment just prior to assembly. To produce the bifurcated stent 250 shown in FIGS. 11B and 12B, edge 272 is connected to edge 149 via weld run 292 and edge 278 is connected to edge 147 via weld run 293 so that first stem half 265' and second stem half 265" form stem 265. FIG. 12B is a cross-sectional end view of the stent shown in FIG. 11B. FIG. 12C shows an alternative pattern that may be used in place of the patterns shown in FIGS. 7 and 7B.

Figure 13:
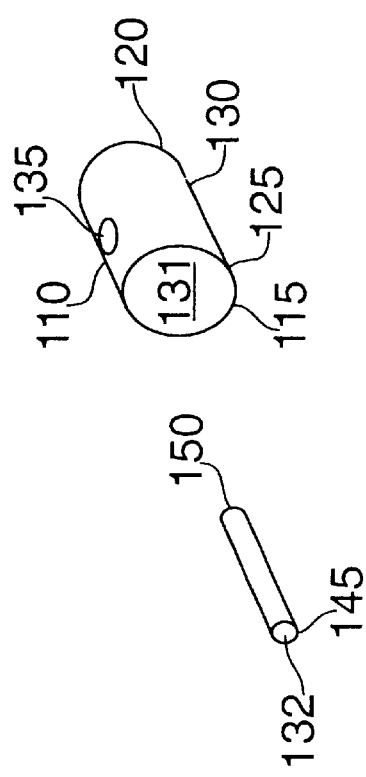
FIG. 13 shows a stem and first leg portion and a second leg portion used to form another embodiment of a bifurcated stent manufactured in accordance with this invention.
Figure 14:
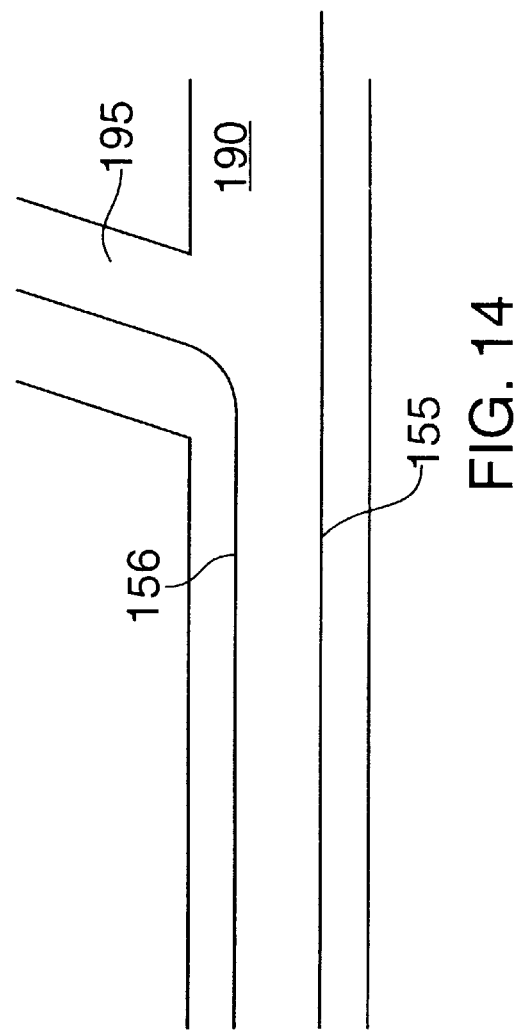
FIG. 14 shows guide wires disposed in the trunk lumen and branch lumen to be treated.
Figure 15:
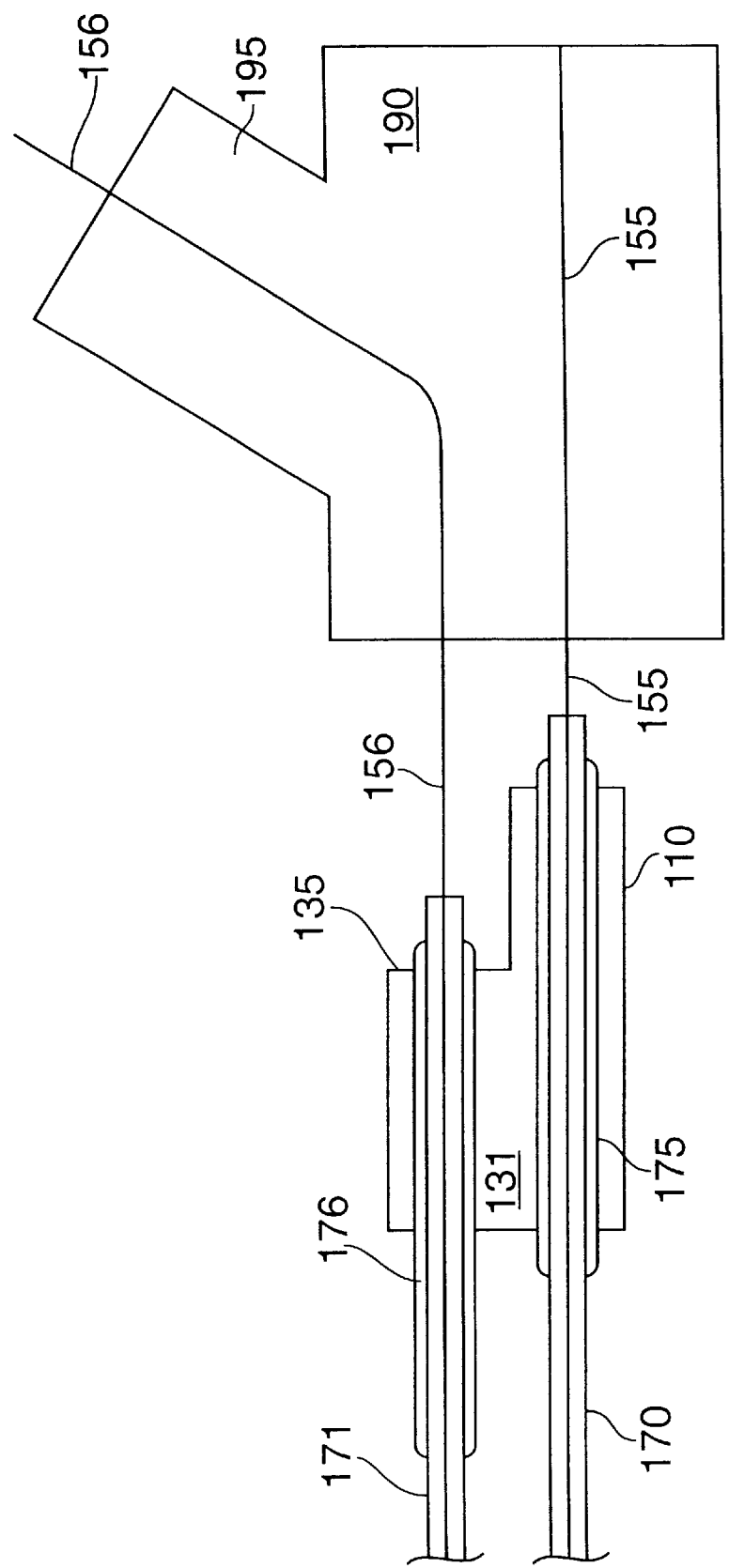
FIG. 15 shows the stem and first leg portion shown in FIG. 13 disposed on catheters and guide wires prior to introduction into the lumen to be treated.
Figure 16:
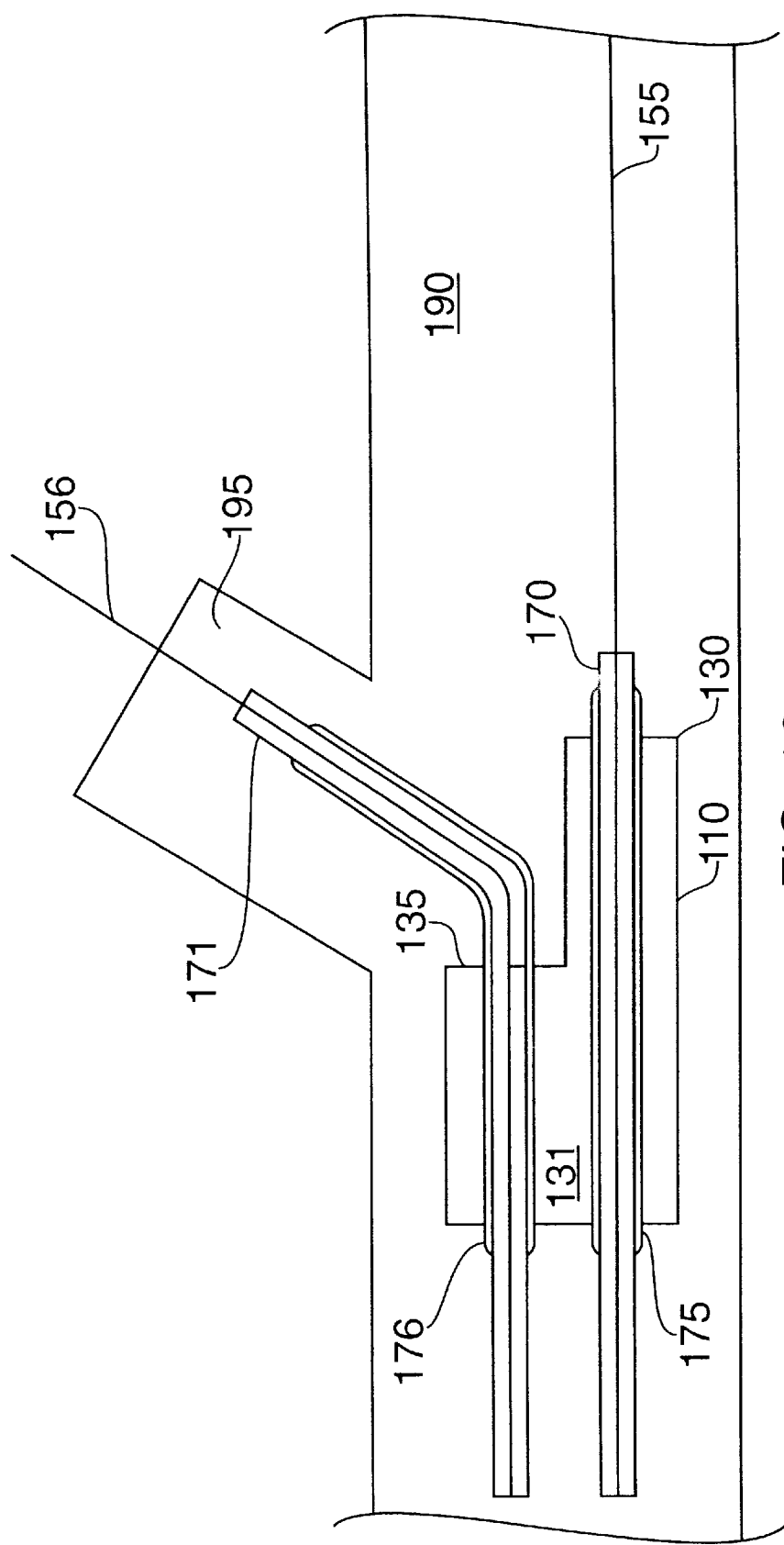
FIG. 16 shows the stem and first leg portion shown in FIG. 13 after it has been delivered to the bifurcation to be treated and prior to its expansion.
Figure 17:
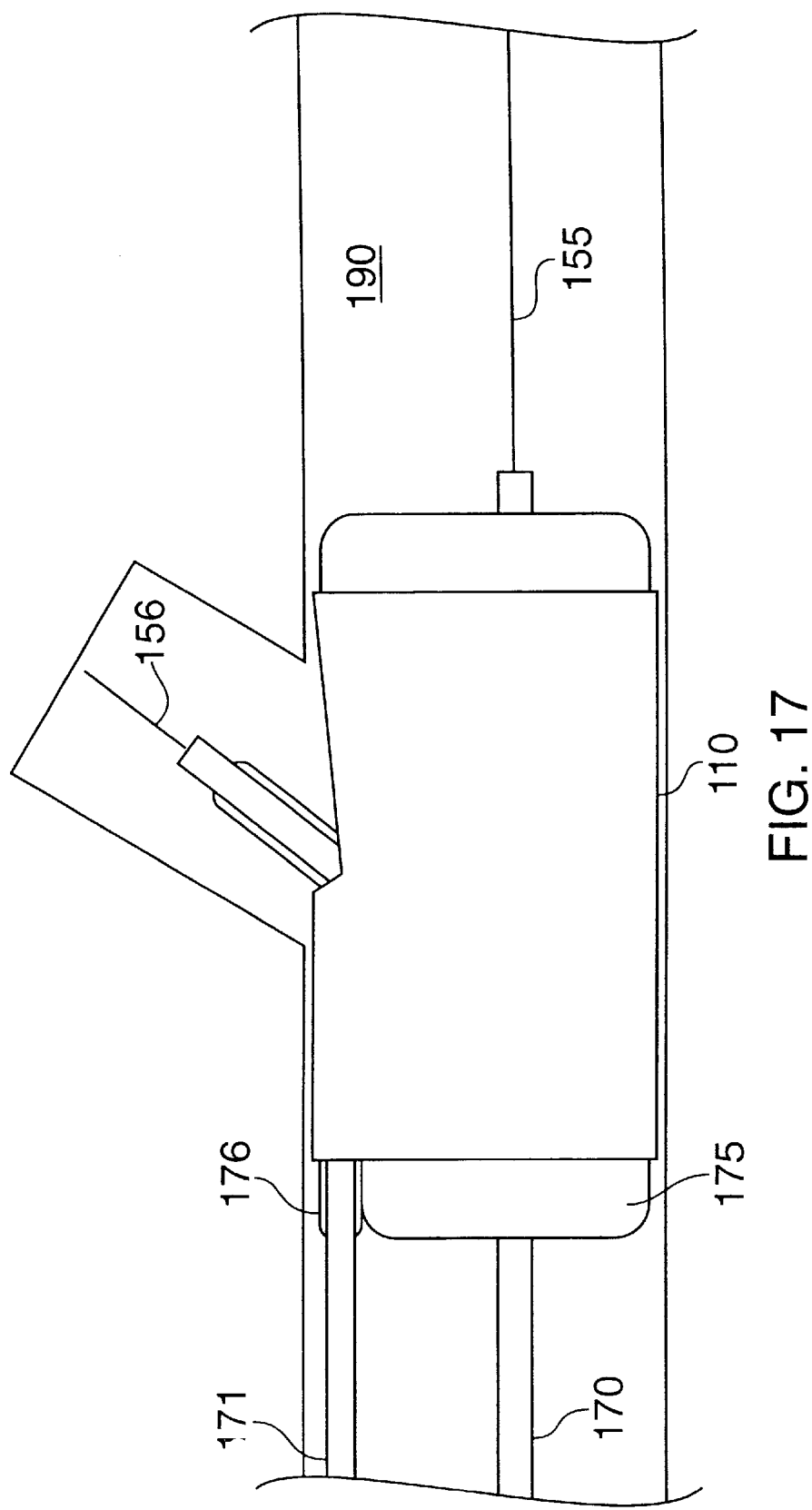
FIG. 17 shows the second leg portion shown in FIG. 16 after it has been expanded.
Figure 18:
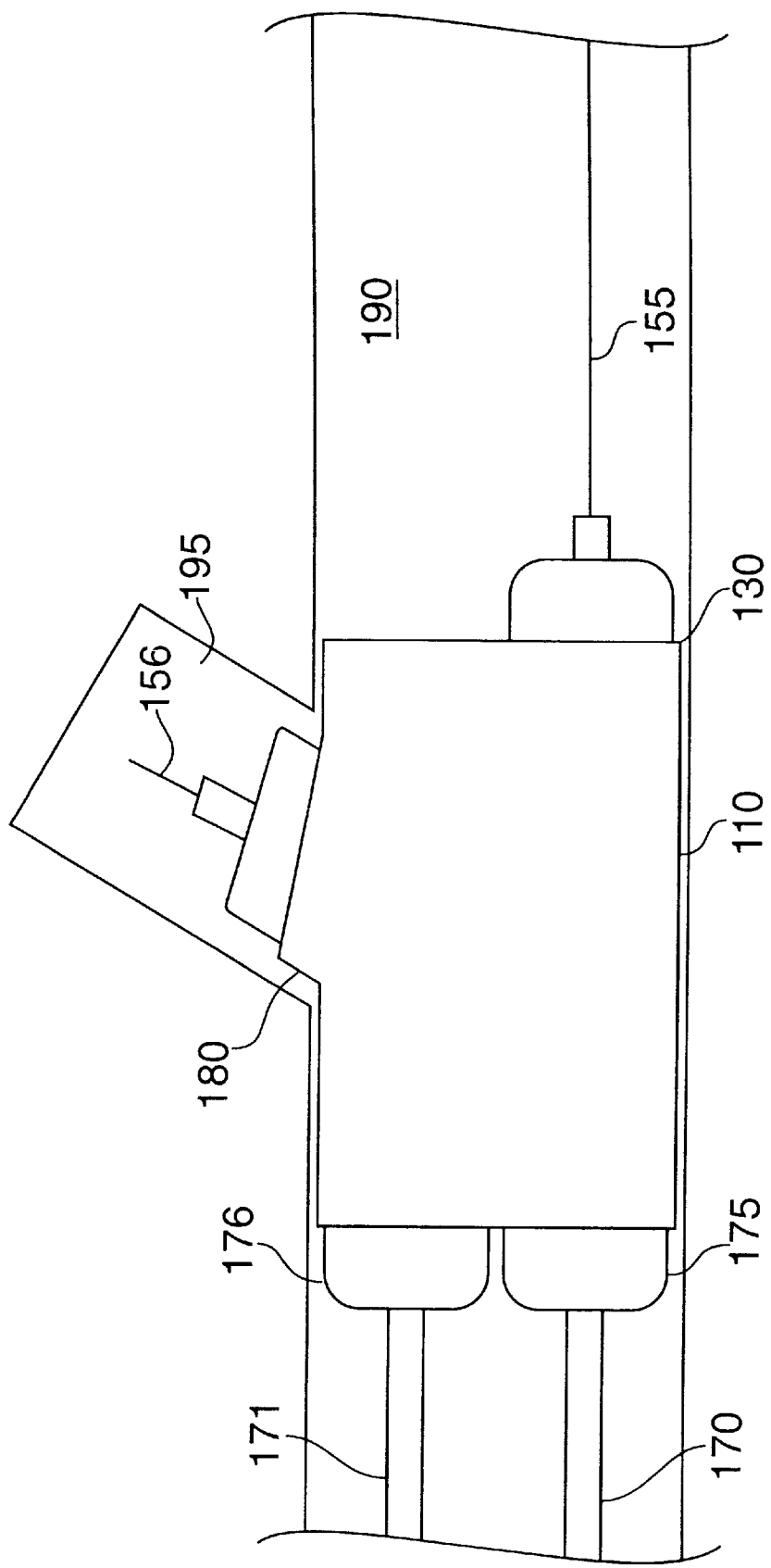
FIG. 18 shows expansion of the branch aperture.

A third embodiment of this invention comprises two portions which are deployed serially in two steps and assembled within the patient to form a bifurcated stent. FIG. 13 shows stem and first leg portion 110 provided with a longitudinal bore 131 and having a proximal end 115 defining a stem portion 125 and a distal end 120 defining a first leg portion 130. Second leg portion 140 is provided with a longitudinal bore 132 and has a proximal end 145 and a distal end 150. Stem and first leg portion 110 and second leg portion 140 may be sized and patterned or etched as previously discussed. A branch aperture 135 is disposed between the proximal end 115 and the distal end 120 of stem and first leg portion 110. The branch aperture 135 is sized to receive second leg portion 140 and is adapted to engage and secure the second leg portion 140 when it has been expanded within the branch aperture 135. Second leg portion 140 is sized and adapted to engage and be secured into branch aperture 135 upon expansion. FIGS. 14 to 21 show how the bifurcated stent is assembled within a bifurcated lumen. As shown in FIGS. 14 to 21, the area to be treated is a bifurcated lumen having a first or trunk lumen 190 and a second or branch lumen 195. As shown in FIG. 14, a first guide wire 155 is introduced into the trunk lumen 190 and a second guide wire 156 is introduced into the branch lumen 195. As shown in FIG. 15, a balloon expandable stem and first leg portion 110 is disposed on the tip of a first balloon catheter 170 so that the balloon 175 is disposed within longitudinal bore 131. A second balloon catheter 171 is then introduced into longitudinal bore 131 of stem and first leg portion 110 and is advanced so that the balloon 176 is disposed within aperture 135. First catheter 170 is mounted on first guide wire 155 and second catheter 171 is mounted on second guide wire 156. As shown in FIG. 16, the unexpanded stem and first leg portion 110 is guided to the area to be treated so that first leg portion 130 is disposed within trunk lumen 190 and branch aperture 135 communicates with branch lumen 195. Guide wire 156 facilitates the orientation of the branch aperture 135 with the branch lumen 195. The size of the conventional catheters and balloons is not to scale and details well known to those skilled in the art have been omitted for clarity. Balloon 175 is inflated which causes the stem and first leg portion 110 to expand, as shown in FIG. 17, to secure it in the desired position. After expansion, the external wall of stem and first leg portion 110 would contact the interior walls of trunk lumen 190, however, a gap has been intentionally left for clarity. The balloon 175 on first catheter 170 is left inflated and the balloon 176 on second catheter 171 is then inflated to enlarge the branch aperture 135 as shown in FIG. 18. As the branch aperture 135 is enlarged a portion of the stent defining the branch aperture 135 is pushed outward to form a branch securing lip 180.

Figure 19:
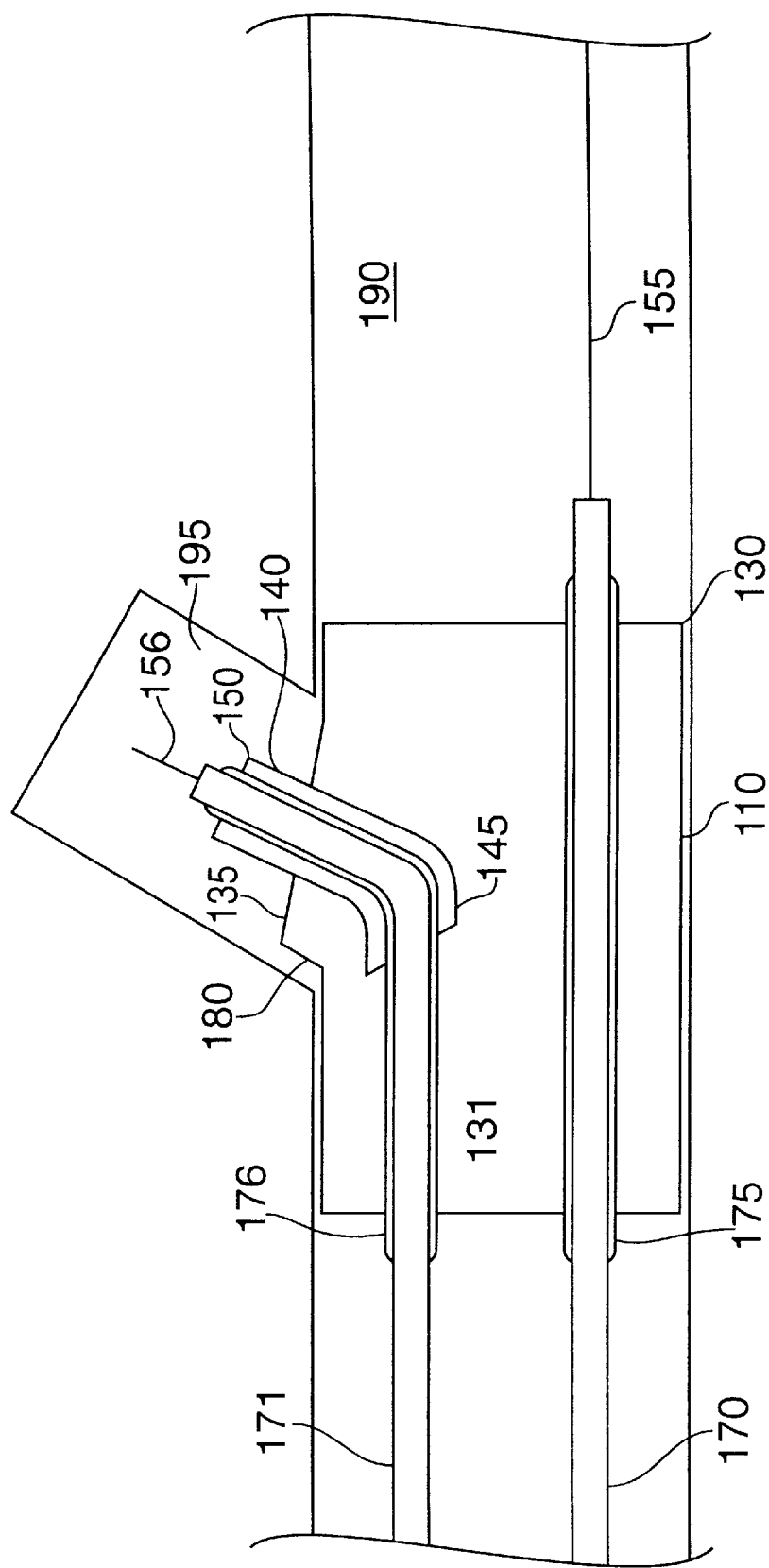
FIG. 19 shows the unexpanded second leg portion disposed in the branch aperture.
Figure 20:
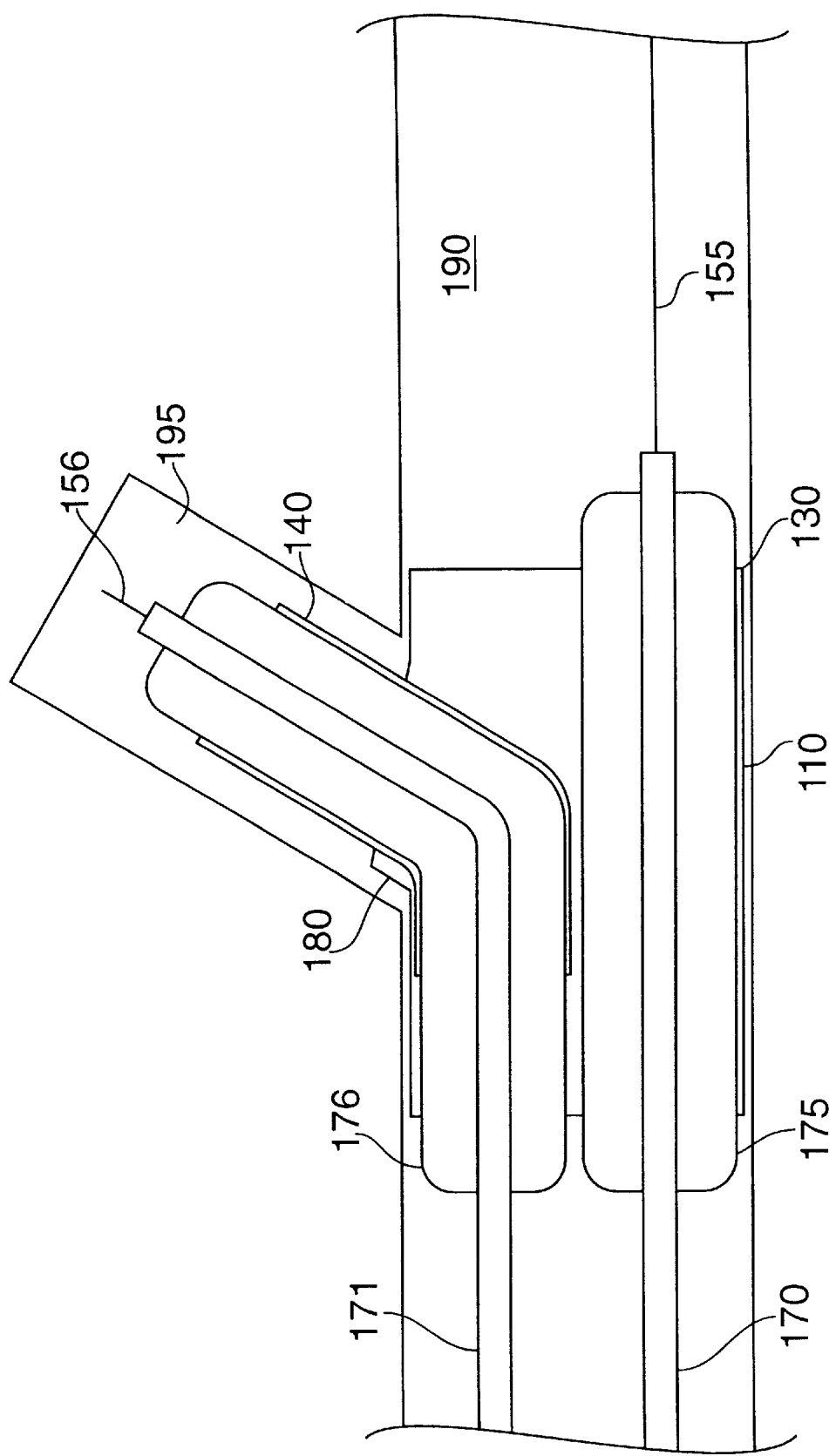
FIG. 20 shows the expansion of the second leg portion shown in FIG. 19.
Figure 21:
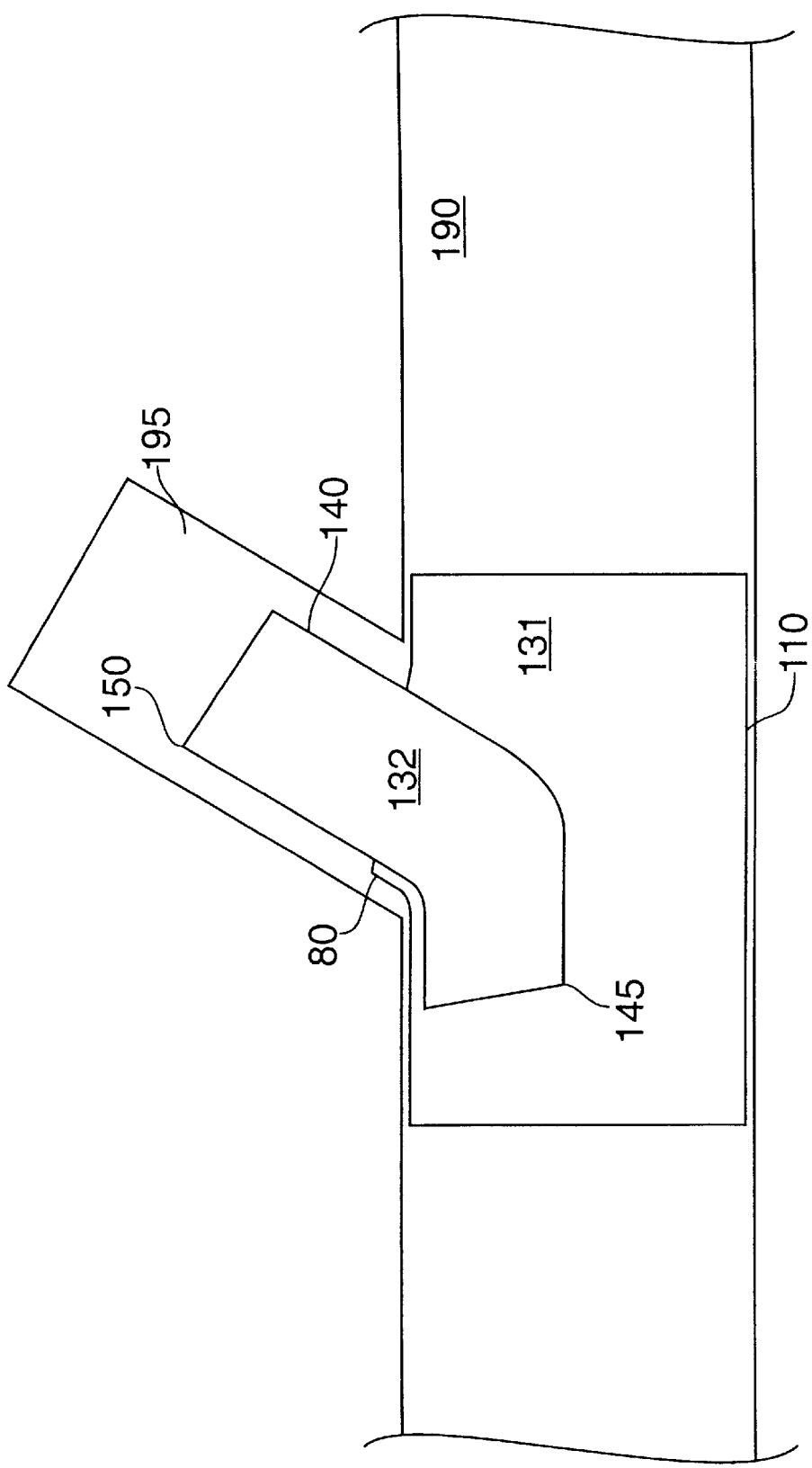
FIG. 21 shows the assembled bifurcated stent disposed in the bifurcated lumen to be treated.

Balloons 175 and 176 are deflated, second catheter 171 is withdrawn, and second guide wire 156 is left in place in the branch lumen 195. Second leg portion 140 is then applied to second catheter 171 so that balloon 176 is disposed in longitudinal bore 132 and second catheter 171 is then applied to second guide wire 156. Second leg portion 140 is then guided to, and introduced into, the longitudinal bore 131 of the stem and first leg portion 110 and is advanced and passed through branch aperture 135 so that the distal end 150 of the second leg portion 140 protrudes into the branch lumen 195 and the proximal end 145 communicates with longitudinal bore 131, as shown in FIG. 19. The balloon 176 on second catheter 171 is partially inflated and the balloon 175 on first catheter 170 is then partially inflated to a pressure substantially equal to the pressure in balloon 176. Both balloons 175 and 176 are then simultaneously inflated to substantially equal pressures. As shown in FIG. 20, inflation of the balloon 176 on second catheter 171 causes second leg member 140 to expand so that its external walls engage and are secured to the area surrounding aperture 135. Inflation of the balloon 175 on the first catheter 170 prevents stem and first leg portion 110 from collapsing when balloon 176 is inflated. After expansion, the external walls of second leg 140 would contact the inner wall of lumen 195, however, a gap has been intentionally left for clarity. The balloons 175 and 176 are deflated, catheters 170 and 171 and guide wires 155 and 156 are withdrawn, and the assembled bifurcated stent 160 is left in place as shown in FIG. 21.

Figure 22:
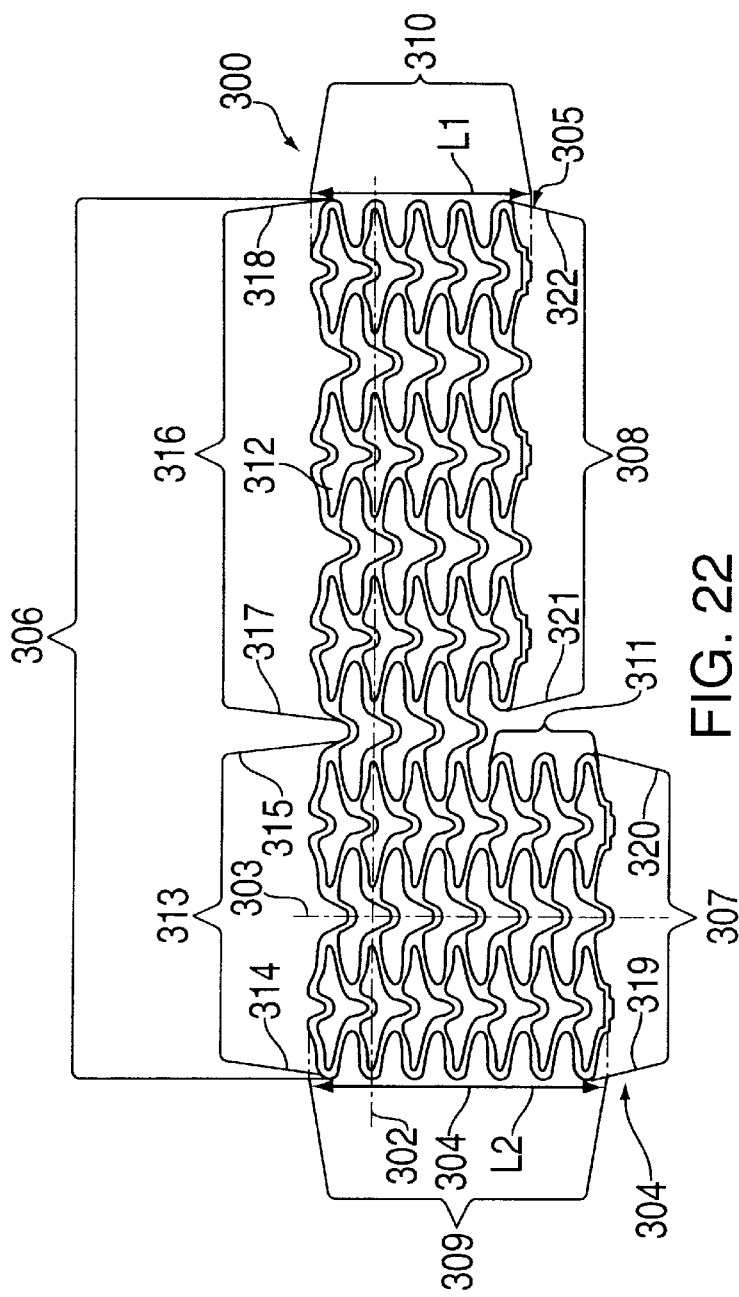
FIG. 22 shows a sheet used to form a first expandable tubular member.

FIGS. 22 to 31 show an especially preferred method of making bifurcated stent in accordance with the invention. FIG. 22 shows a sheet 300 used to form a first expandable tubular member 301. The sheet 300 has a longitudinal axis 302, a circumferential axis 303, a proximal end 304, a distal end 305, a first side 306, a second side 307, a third side 308, a fourth side 309, a fifth side 310, and a sixth side 311. The sheet 300 may be provided with a variety of patterns, however, in a preferred embodiment the sheet 300 is provided with a plurality of expandable cells 312 adapted to be substantially flexible prior to expansion of the first tubular member 301 and substantially rigid after expansion of the first tubular member 301. In an especially preferred embodiment the flexible cells 312 of the sheet 300 are substantially uniform as shown in FIG. 22.

The first side 306 of the sheet 300 has a proximal portion 313 having a proximal end 314 and a distal end 315. The first side 306 also has a distal portion 316 having a proximal end 317 and a distal end 318.

The second side 307 of the sheet 300 has a proximal end 319 and a distal end 320 and is disposed between the proximal end 304 of the sheet 300 and the distal end 305 of the sheet 300.

The third side 308 of the sheet 300 has a proximal end 321 and a distal end 322 and is disposed between the distal end 320 of the second side 307 and the distal end 305 of the sheet 300.

The fourth side 309 of the sheet 300 is disposed between the proximal end 314 of the proximal portion 313 of the first side 306 and the proximal end 319 of the second side 307.

The fifth side 310 of the sheet 300 is disposed between the distal end 318 of the distal portion 316 of the first side 306 and the distal end 322 of the third side 308 and is provided with a length L1 that is shorter than the length L2 of the fourth side 309. In a preferred embodiment, the length L1 of the fifth side 310 and the length L2 of the fourth side 309 are in a ratio of 10 about 5:7, i.e., the fifth side 310 has a length L1 that is about 70% of the length L2 of the fourth side 309. In an especially preferred embodiment the sheet 300 is etched with a plurality of substantially uniform cells 312 as previously discussed and the number of cells disposed along the circumferential axis 303 of the fifth side 310 and the number of cells disposed along the circumferential axis 303 of the fourth side 309 are in a ratio of about 5:7.

A sixth side 311 is disposed between the second side 307 and the third side 308. In an especially preferred embodiment, the first side 306, second side 307, and third side 308 are substantially parallel to each other and the fourth side 309, fifth side 310, and sixth side 311 are substantially parallel to each other and the first side 306, second side 307, and third side 308 are substantially perpendicular to the fourth side 309, fifth side 310, and sixth side 311.

Figure 23:
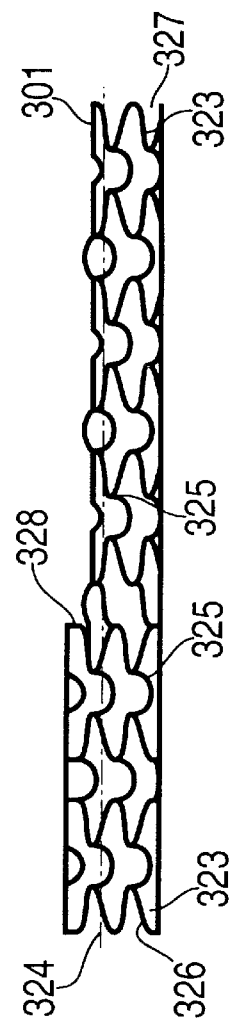
FIG. 23 shows the sheet of FIG. 22 after it has been formed into a first expandable tubular member.
Figure 24:
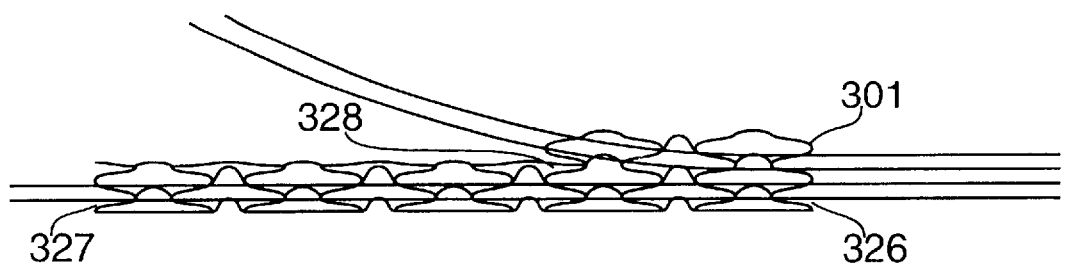
FIG. 24 shows the first expandable tubular member of FIG. 23 with catheters inserted into the longitudinal bore and the side branch aperture.
Figure 26:
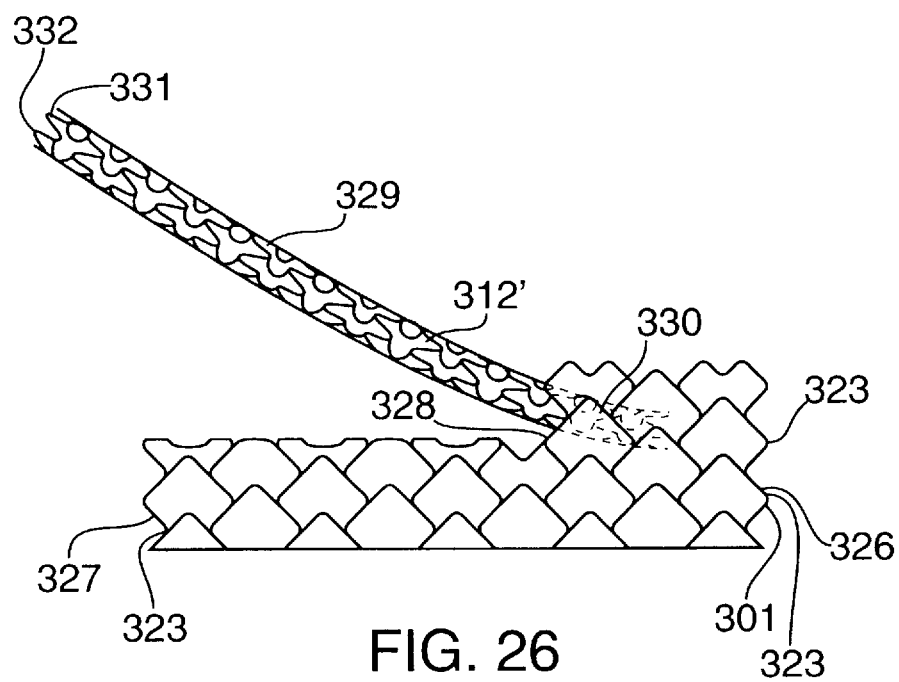
FIG. 26 shows the first expandable tubular member of FIG. 24 after expansion with an unexpanded second tubular member disposed in the side branch aperture.

To make the first expandable tubular member 301, the second side 307 of the sheet 300 is attached via attaching means to the proximal portion 313 of the first side 306 of the sheet 300 and the third side 308 of the sheet 300 is attached via attaching means to the distal portion 316 of the first side 306 of the sheet 300 to form a first expandable tubular member 301 having a longitudinal bore 323 defining a longitudinal axis 324 as shown in FIG. 23. The attaching step may be carried out utilizing a variety of attaching means well known to those skilled in the art as suitable for this purpose, however, in a preferred embodiment the attaching step is carried out utilizing screwing, crimping, soldering, welding, or spot welding. In the embodiment shown in FIG. 23 spot welding 325 has been utilized. After the sides have been attached as discussed above, the fourth side 309 defines a proximal tubular member aperture or stent aperture 326 communicating with the longitudinal bore 323, and the fifth side 310 defines a distal tubular member aperture or stent aperture 327 communicating with the longitudinal bore 323 as shown in FIGS. 23 and 26. The sixth side 311 and the proximal end 321 of the third side 308 and the proximal end 317 of the distal portion 316 of the first side 306 define a side branch aperture 328 (as shown in FIGS. 23–26) sized and adapted to receive and secure a second expandable tubular member 329 (shown in FIGS. 26–27). The branch aperture 328 has a diameter D1 that is larger than the diameter D2 of the unexpanded stent, i.e., the branch aperture 328 is larger than the proximal and distal apertures 326 and 327 of the first tubular member 301 both before and after the tubular member 301 is expanded.

The first expandable tubular member 301 is then delivered to bifurcated vessel having a first lumen and a second lumen so that the first expandable tubular member is disposed within the first lumen and the branch aperture communicates with the second lumen. In a preferred embodiment, delivery is via a balloon catheter as previously discussed. After it has been positioned, the first expandable tubular member is expanded in an amount sufficient to secure the first expandable tubular member in the first lumen.

A second expandable tubular member 329 is then prepared having a proximal end 330 and a distal end 331 and having longitudinal bore 332 therethrough. The second expandable tubular member 329 (shown in FIGS. 25, 26, and 27) may be patterned in the same way as the sheet 300 as previously discussed. In a preferred embodiment the cells 312 of the sheet 300 used to make the first expandable tubular member 301 and the cells 312' of the second expandable tubular member 329 are substantially uniform.

Figure 25:
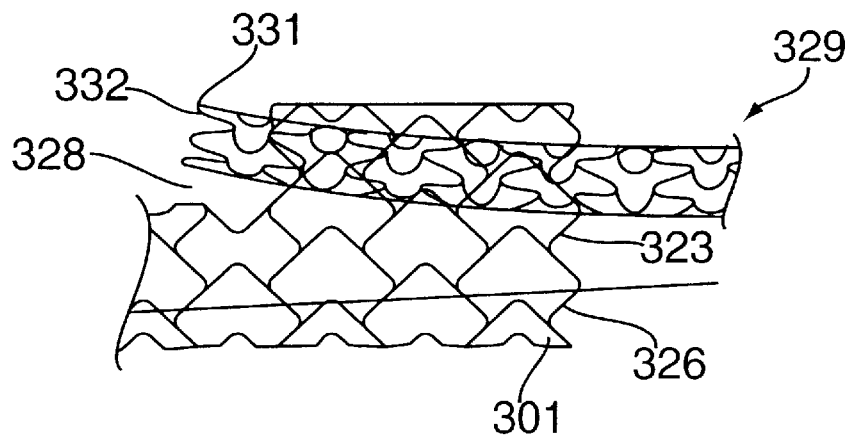
FIG. 25 shows the first expandable tubular member of FIG. 24 after expansion with an unexpanded second tubular member being introduced into the side branch aperture.
Figure 27:
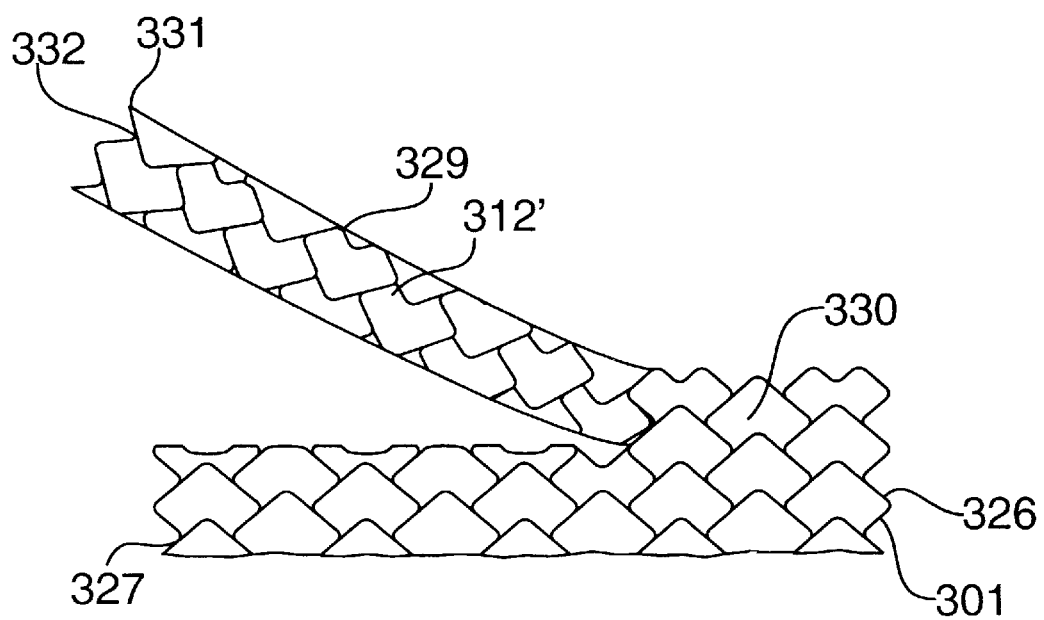
FIG. 27 shows the second tubular member of FIG. 26 after it has been expanded.

The second expandable tubular member 329 is delivered into the longitudinal bore 323 of the first tubular member 301, as shown in FIG. 25, and is advanced into and beyond the branch aperture 328, as shown in FIG. 26, so that the distal end 331 of the second expandable tubular member 329 is disposed within the second lumen and the proximal end 330 of the second expandable tubular member 329 is disposed within the longitudinal bore 323 of the first tubular member 301. The second expandable tubular member 329 is then expanded in an amount sufficient to secure the second expandable tubular member 329 within the second lumen and within the branch aperture 328 of the first tubular member 301 as shown in FIG. 27.

Among the advantages that this embodiment provides is that this stent provides a large branch aperture that facilitates the introduction of the second tubular member into the side branch or second lumen. In addition, this stent is especially suitable for the performance of serial bifurcation stenting and also for stenting around a side branch before it is occluded.

Figure 28:
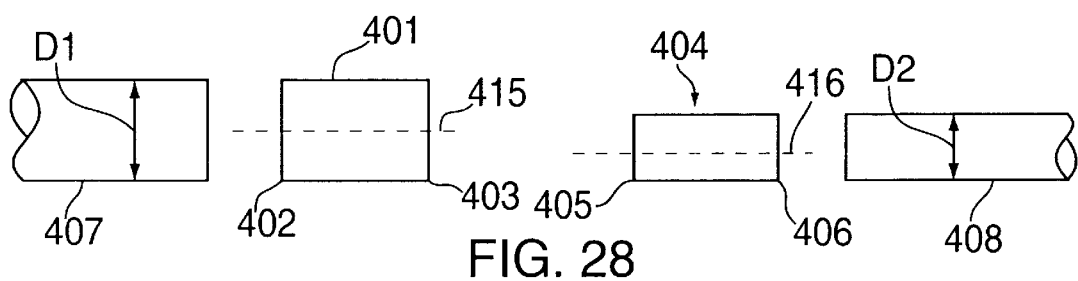
FIG. 28 shows a side view of a proximal member and a distal member used to make an alternative embodiment of the invention.
Figure 29:
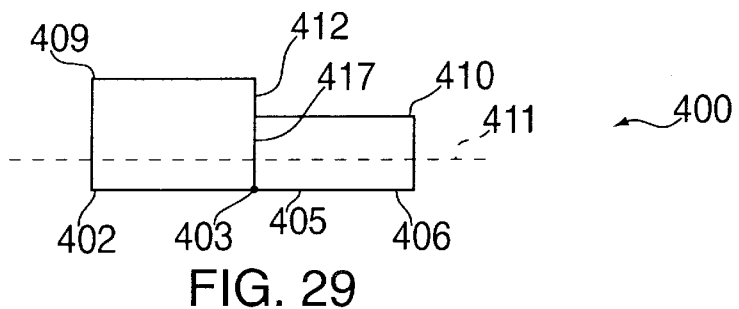
FIG. 29 shows the proximal and distal members of FIG. 28 after they have been connected to form a first expandable tubular member.
Figure 30:
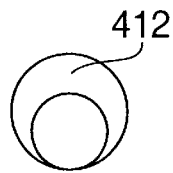
FIG. 30 is an end view of FIG. 29.
Figure 30A:
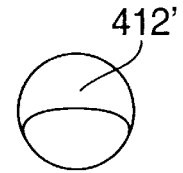
FIG. 30A is an end view of FIG. 29 showing an alternative embodiment in which a portion of the proximal member and a portion of the distal member have been deformed prior to being attached.
Figure 31:
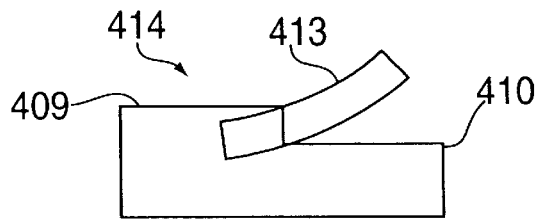
FIG. 31 shows the first expandable tubular member of FIG. 29 with a second expandable tubular member disposed within the side branch aperture.

FIGS. 28 to 31 shown an alternative embodiment and alternative method of making the first tubular member shown in FIGS. 23–27. In this embodiment the first tubular member 400(shown in FIG. 29) is comprised of a proximal member 401 having a proximal end 402 and a distal end 403 and a distal member 404 having a proximal end 405 and a distal end 406 as shown in FIG. 28. The proximal member 401 has a longitudinal bore 415 and is cut from a first tube 407 having first cross-sectional diameter D1. The distal member 404 has a longitudinal bore 416 and is cut from a second tube 408 having a second cross-sectional diameter D2. D2 is smaller than D1. The tubes 401 and 404 may be etched or patterned as previously discussed before the proximal member 401 and distal member 404 are cut from the tubes 407 and 408. Alternatively, the proximal and distal members 401 and 404 may be etched or patterned after the proximal and distal members 401 and 404 have been cut from the tubes 407 and 408. To make the first tubular member 400, a portion of the distal end 403 of the proximal member 401 is attached via attaching means 417 to a portion of the proximal end 405 of the distal member 404 to form a first tubular member 400 having a proximal end 409 and a distal end 410 and a longitudinal bore therethrough 411 as shown in FIG. 29. The members 401 and 404 may be attached utilizing a variety of attaching means 417 as previously discussed, however, in a preferred embodiment the attaching means utilized is welding. In an especially preferred embodiment spot welding is utilized. Because D2 is less than D1 the unattached portion of the distal end 403 of the proximal portion 401 and the unattached portion of the proximal end 405 of the distal portion 404 define a branch aperture 412 as shown in FIG. 29 and FIG. 30 (which is an end view of FIG. 29). In some applications it may be desirable to have a greater portion of the distal end 403 of the proximal member 401 and the proximal end 405 of the distal member 404 contact each other before they are attached in order to increase the strength of the first tubular member 400. This may be accomplished by, e.g., by distorting, aligning, and contacting a greater surface area of the distal end 403 of the proximal member 401 and a greater surface area of the proximal end 405 of the distal member 404 prior to attaching the distal end 403 to the proximal end 405. FIG. 30A is an end view of this embodiment and shows that a greater surface area of the distal end 403 and the proximal end 405 are attached when compared to the embodiment shown in FIG. 30. FIG. 30A also shows that in this embodiment the branch aperture 412' is larger than the branch aperture 412 shown in FIG. 30. A second tubular member 413 may then be introduced into the branch aperture 412 and 412' and as previously discussed is expanded and secured so that a portion of the second tubular member 413 communicates with longitudinal bore 411 to form a bifurcated stent 414 (shown in FIG. 31).

Figure 32:
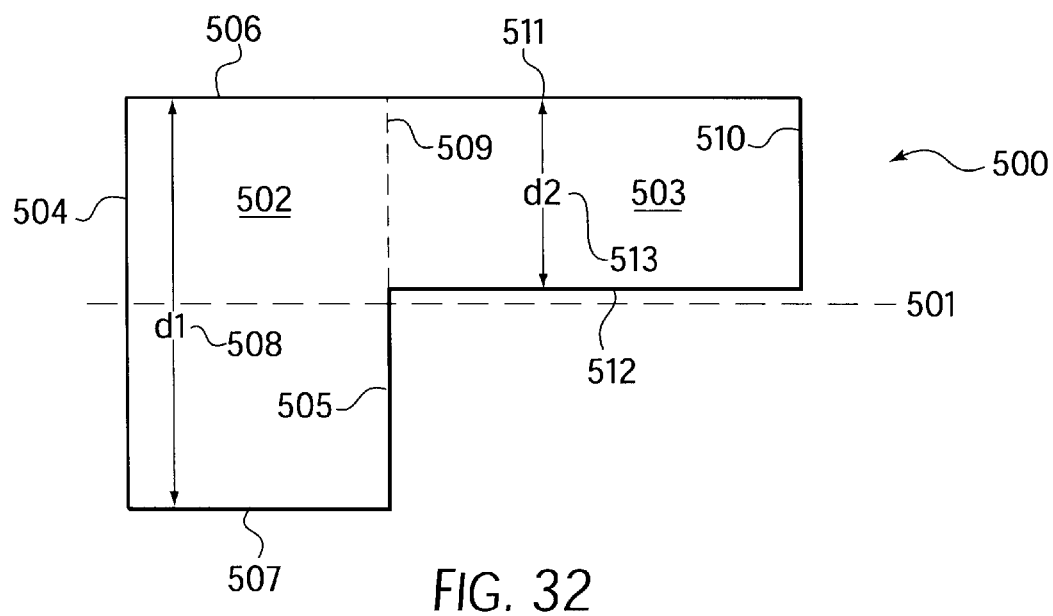
FIG. 32 shows a sheet used to form a stent in accordance with the invention.

FIG. 32 shows a simplified version of the "L" shaped sheet shown in FIG. 22. The sheet 500 of FIG. 32 may be described as a sheet having a longitudinal axis 501 and a first portion 502 and a second portion 503. The first portion 502 has a proximal end 504 and a distal end 505 and a first lateral side 506 and a second lateral side 507. The lateral sides 506 and 507 of the first portion 502 are substantially parallel to the longitudinal axis 501 and are disposed apart from each other a first distance d1 508. The second portion 503 has a proximal end 509 and a distal end 510 and a first lateral side 511 and a second lateral side 512. The lateral sides 511 and 512 of the second portion 503 are substantially parallel to the longitudinal axis 501 and are disposed apart from each other a second distance d2 513 that is less than the first distance d1 508. The proximal end 509 of the second portion 503 communicates with the distal end 505 of the first portion 502.

Making a stent utilizing the sheet of FIG. 32 comprises the steps of: connecting the first lateral side 506 of the first portion 502 to the second lateral side 507 of the first portion 502 and connecting the first lateral side 511 of the second portion 503 to the second lateral side 512 of the second portion 503 to form a first tubular member 301 having a longitudinal bore 323 therethrough as shown in FIG. 23. A portion of the distal end 505 of the first portion 502 and a portion of the proximal end 509 of the second portion 503 define a side branch aperture 328 as shown in FIG. 23. If it is desired to make a bifurcated stent, a second tubular member 329 having a proximal end 330 and a distal end 331 and a longitudinal bore 332 therethrough may be disposed and secured within the branch aperture 328 of the first tubular member 301 so that the longitudinal bore 332 of the second tubular member 329 is in fluid communication with the longitudinal bore 323 of the first tubular member 301.

Figure 33:
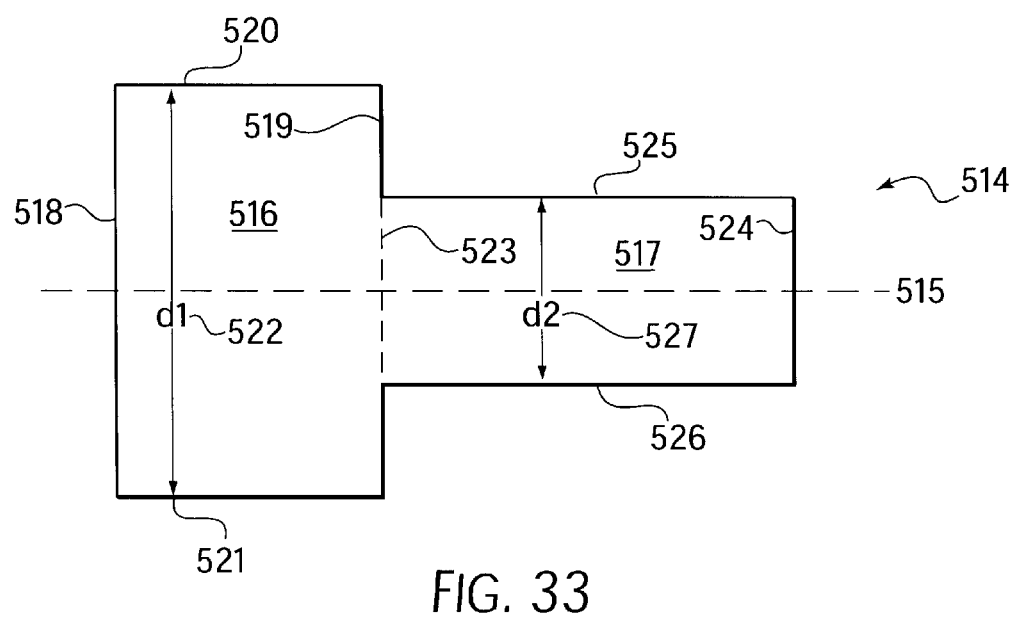
FIG. 33 shows another embodiment of a sheet used to form a stent in accordance with the invention.
Figure 33A:
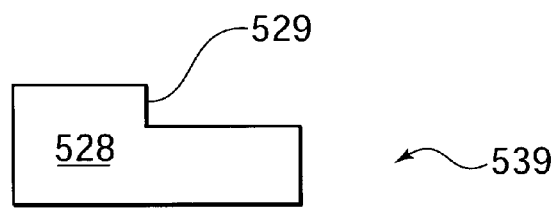
FIG. 33A shows a stent manufactured utilizing the sheet of FIG. 33.

FIG. 33 shows another embodiment of a sheet 514 used to make a stent in accordance with Applicant's invention. FIG. 33 shows a sheet 514 having a longitudinal axis 515 and a first portion 516 and a second portion 517. The first portion 516 has a proximal end 518 and a distal end 519 and a first lateral side 520 and a second lateral side 521. The lateral sides 520 and 521 of the first portion 516 are substantially parallel to the longitudinal axis 515 and are disposed apart from each other a first distance d1 522. The second portion 517 has a proximal end 523 and a distal end 524 and a first lateral side 525 and a second lateral side 526. The lateral sides 525 and 526 of the second portion 517 are substantially parallel to the longitudinal axis 515 and are disposed apart from each other a second distance d2 527 that is less than the first distance d1 522. The proximal end 523 of the second portion 517 communicates with the distal end 519 of the first portion 516. Making a stent utilizing the sheet of FIG. 33 comprises the steps of connecting the first lateral side 520 of the first portion 516 to the second lateral side 521 of the first portion 516 and connecting the first lateral side 525 of the second portion 517 to the second lateral side 526 of the second portion 517 to form a first tubular member 539 having a longitudinal bore 528 therethrough as shown in FIG. 33A. A portion of the distal end 519 of the first portion 516 and a portion of the proximal end 523 of the second portion 517 define a side branch aperture 529. If it is desired to make a bifurcated stent, a second tubular member having a longitudinal bore may be disposed and secured within the branch aperture of the first tubular member so that the longitudinal bore of the second tubular member is in fluid communication with the longitudinal bore of the first tubular member as previously discussed.

Figure 34:
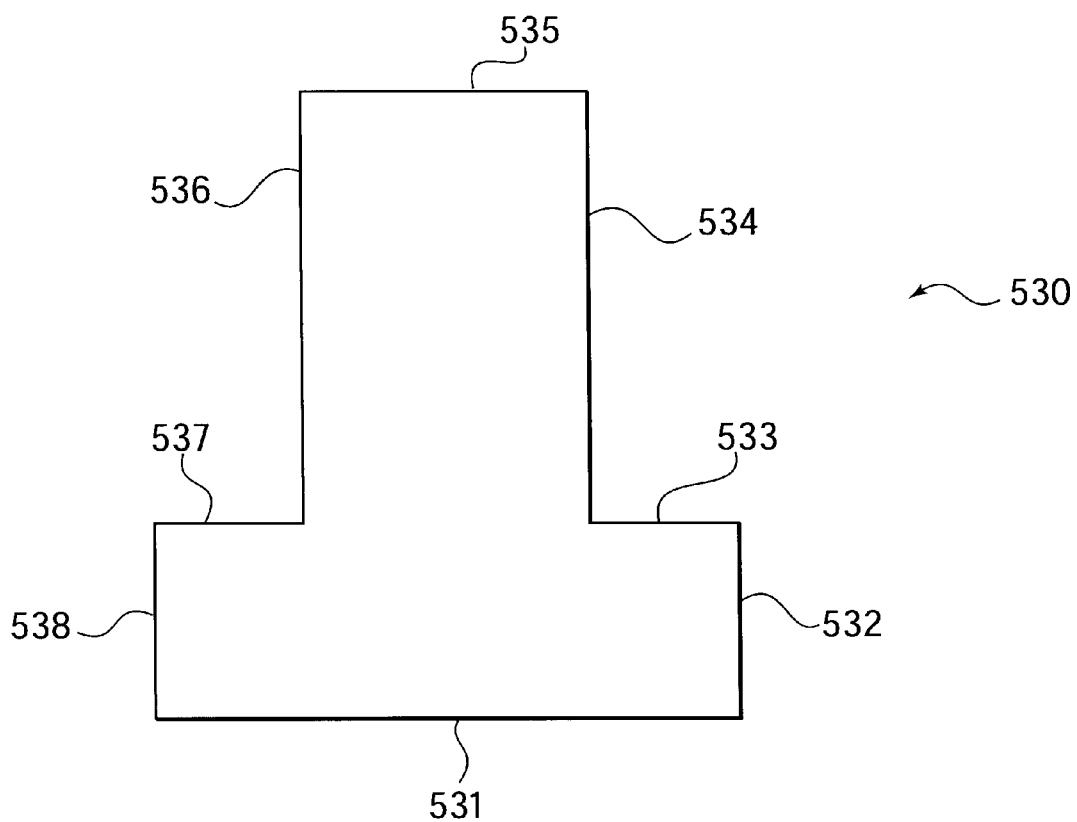
FIG. 34 shows a sheet used to form a stent in accordance with the invention.

The sheet of FIG. 33 may also be described as a sheet 530 having a first side 531, a second side 532, a third side 533, a fourth side 534, a fifth side 535, a sixth side 536, a seventh side 537, and an eighth side 538 as shown in FIG. 34. Making a stent 539 utilizing the sheet shown in FIG. 34 comprises the steps of connecting the second side 532 to the eighth side 538 and connecting the fourth side 534 to the sixth side 536 to form a stent 539 having a longitudinal bore 528 therethrough and wherein the third side 533 and the seventh side 537 define a branch aperture 529 disposed between the first side 531 and the fifth side 535 as shown in FIG. 33A. If it is desired to make a bifurcated stent, a second tubular member having a longitudinal bore is disposed and secured within the branch aperture of the first tubular member so that the longitudinal bore of the second tubular member is in fluid communication with the longitudinal bore of the first tubular member as previously discussed.

An especially preferred method of making a bifurcated stent comprises the steps of preparing a first expandable tubular member having a proximal end and a distal end and a longitudinal bore therethrough. The first tubular member is provided with a branch aperture disposed between the proximal end and the distal end. The branch aperture communicates with the longitudinal bore of the first expandable tubular member and the aperture is sized and adapted to receive and secure a second expandable tubular member. The first expandable tubular member is delivered to a bifurcated vessel having a first lumen and a second lumen so that the first expandable tubular member is disposed within the first lumen and the branch aperture communicates with the second lumen. The branch aperture is widened in an amount sufficient to further align the branch aperture with the second lumen. As specific applications dictate, the portion of the first expandable tubular member defining the branch aperture may be adapted to form a branch securing lip when the branch aperture is expanded a sufficient amount. The first expandable tubular member is then expanded an amount sufficient to secure the first expandable tubular member in the first lumen. A second expandable tubular member is prepared having a proximal end and a distal end having longitudinal bore therethrough. The second expandable tubular member is delivered into the branch aperture so that the distal end of the second expandable tubular member is disposed within the second lumen and the proximal end of the second expandable tubular member is disposed within the branch aperture of the first tubular member and so that the longitudinal bore of the second expandable tubular member is in fluid communication with the longitudinal bore of the first longitudinal tubular member. The second expandable tubular member is then expanded in an amount sufficient to secure the second expandable tubular member within the second lumen and within the branch aperture of the first expandable tubular member.

Still another especially preferred method of making a bifurcated stent comprises the steps of delivering a first guide wire into the first lumen of a bifurcated vessel having a first lumen and a second lumen and delivering a second guide wire into the second lumen of the bifurcated vessel. A first expandable tubular member is prepared having a proximal end and a distal end and a longitudinal bore therethrough. The first expandable tubular member is provided with a branch aperture disposed between the proximal end and the distal end. The branch aperture communicates with the longitudinal bore and the branch aperture is sized and adapted to receive and secure a second expandable tubular member. The first expandable tubular member is mounted on a first balloon catheter and the first balloon catheter is mounted on the first guide wire. The first expandable tubular member is delivered to the first lumen of the bifurcated vessel so that the first expandable tubular member is disposed within the first lumen and the branch aperture communicates with the second lumen. A second balloon catheter is mounted on the second guide wire and the balloon portion of the second balloon catheter is delivered into the sidebranch aperture. The second balloon catheter is inflated to widen the branch aperture in an amount sufficient to form a branch securing lip and to further align the branch aperture with the second lumen. The first balloon catheter is then inflated to expand the first expandable member in an amount sufficient to secure the first expandable member in the first lumen. The first and second balloon catheters are deflated and the second balloon catheter is removed. A second expandable tubular member is prepared having a proximal end and a distal end having longitudinal bore therethrough. The second expandable tubular member is mounted on the second balloon catheter. The second expandable tubular member, mounted on the second balloon catheter, is delivered into the branch aperture so that the distal end of the second expandable tubular member is disposed within the second lumen and the proximal end of the second expandable tubular member is disposed within the branch aperture of the first tubular member and so that the longitudinal bore of the second expandable tubular member is in fluid communication with the longitudinal bore of the first longitudinal member. The first balloon catheter is inflated. The second balloon catheter is inflated to expand the second expandable tubular member in an amount sufficient to secure the second expandable tubular member within the second lumen and within the branch aperture. As specific applications dictate, the portion of the first tubular stent defining the side branch aperture may be adapted to form a branch securing lip when the branch aperture is expanded a sufficient amount. In one embodiment, the first balloon catheter is inflated before the second balloon catheter is inflated and the first balloon catheter is left inflated until the second expandable tubular member is secured within the branch aperture by the second balloon catheter. In another embodiment, the first balloon catheter and the second balloon catheter are inflated simultaneously.

What is claimed is:

1. A stent comprising:

a first tubular member having a longitudinal bore formed from a sheet having a first side, a second side, a third side, a fourth side, a fifth side, a sixth side, a seventh side, and an eighth side, the second side connected to the eighth side and the fourth side connected to the sixth side, the third side and the seventh side defining a branch aperture disposed between the first side and the fifth side.

2. The stent of claim 1, further comprising, a second tubular member having a longitudinal bore disposed and secured within the branch aperture of the first tubular member, the longitudinal bore of the second tubular member in fluid communication with the longitudinal bore of the first tubular member.

3. A stent comprising:

a sheet having a longitudinal axis and a first portion and a second portion;

the first portion having a proximal end and a distal end and a first lateral side and a second lateral side, the lateral sides of the first portion substantially parallel to the longitudinal axis and disposed apart from each another a first distance;

the second portion having a proximal end and a distal end and a first lateral side and a second lateral side, the lateral sides of the second portion substantially parallel to the longitudinal axis and disposed apart from each other a second distance that is less than the first distance, the proximal end of the second portion communicating with the distal end of the first portion; and the first lateral side of the first portion connected to the second lateral side of the first portion and the first lateral side of the second portion connected to the second lateral side of the second portion to form a first tubular member having a longitudinal bore therethrough, a portion of the distal end of the first portion and a portion of the proximal end of the second portion defining a side branch aperture.

4. The stent of claim 3, further comprising:

a second tubular member having a longitudinal bore disposed and secured within the branch aperture of the first tubular member, the longitudinal bore of the second tubular member in fluid communication with the longitudinal bore of the first tubular member.

* * * * *